(12) United States Patent
Bydlinski et al.

(10) Patent No.: US 7,982,056 B2
(45) Date of Patent: Jul. 19, 2011

(54) SUBSTANTIALLY PURE FLUORESCEIN

(75) Inventors: Gregory Bydlinski, Kirkland (CA); Robert Gregg Harris, Fort Worth, TX (US); Britt S. Scott, Burleson, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 701 days.

(21) Appl. No.: 11/949,922

(22) Filed: Dec. 4, 2007

(65) Prior Publication Data

US 2008/0176930 A1  Jul. 24, 2008

Related U.S. Application Data

(60) Provisional application No. 60/869,488, filed on Dec. 11, 2006.

(51) Int. Cl.
*C07D 311/82* (2006.01)
*C07D 311/78* (2006.01)

(52) U.S. Cl. .................... 549/223; 549/224

(58) Field of Classification Search .......... 549/223, 549/224
See application file for complete search history.

(56) References Cited

U.S. PATENT DOCUMENTS

| | | | |
|---|---|---|---|
| 1,965,842 A | 7/1934 | Kranz | |
| 5,188,934 A * | 2/1993 | Menchen et al. | 435/6 |
| 5,637,733 A * | 6/1997 | Sujeeth | 549/223 |
| 6,162,931 A * | 12/2000 | Gee et al. | 549/223 |
| 6,229,055 B1 * | 5/2001 | Klaubert et al. | 568/765 |
| 6,552,199 B1 * | 4/2003 | Daltrozzo et al. | 546/174 |
| 2006/0106234 A1 | 5/2006 | Tran-Guyon et al. | |

FOREIGN PATENT DOCUMENTS

DE  136498  7/1979

OTHER PUBLICATIONS

Yannuzi, et al.; "Effective Differences in the Formulation of Intravenous Fluorescein and Related Side Effects"; Am. J. Ophthalmol. vol. 78(2); pp. 217-221; (1974).
PCT/US2007/086390 partial International Search Report with mailing date Dec. 10, 2008.
Tremayne, et al.; "Structure determination of a complex organic solid from x-ray powder diffraction data by a generalized Monte Carlo method: the crystal structure of red fluorescein"; Angew. Chem. Int. Ed. Engl.; vol. 36, No. 7; pp. 770-772; 1997.
Markuszewski, et al.; "The infrared spectra and structures of the three solid forms of fluorescein and related compounds"; Talanta; vol. 27; pp. 937-946, (1960).
Anthoni, et al.; "Structure of red and orange fluorescein"; Structural Chemistry; vol. 6; No. 3; pp. 161-165; 1995.

* cited by examiner

*Primary Examiner* — Janet L. Andres
*Assistant Examiner* — Raymond Covington
(74) *Attorney, Agent, or Firm* — Michael D. Rein

(57) ABSTRACT

The present invention is directed to an improved process for producing substantially pure fluorescein, as well as to substantially pure fluorescein compositions prepared by the process. The invention is particularly directed to the provision of pharmaceutical compositions for use in angiography. The substantially pure fluorescein produced by the process of the present invention is low in color, low in sodium chloride content, and substantially free of pyridine.

20 Claims, 23 Drawing Sheets

Experimental Design for Purification of Fluorescein:

HPLC Chromatogram of Fluorescein from the LC/MS System

HPLC/MS of Fluorescein

HPLC/MS of Impurity A in Fluorescein Drug Substance

HPLC/MS of Impurity B in Fluorescein Drug Substance

Peak B
$C_{16}H_{12}O_5$
Mol. Wt. = 284
M+H = 285

HPLC/MS of Impurity C in Fluorescein Drug Substance

HPLC/MS of Impurity D in Fluorescein Drug Substance

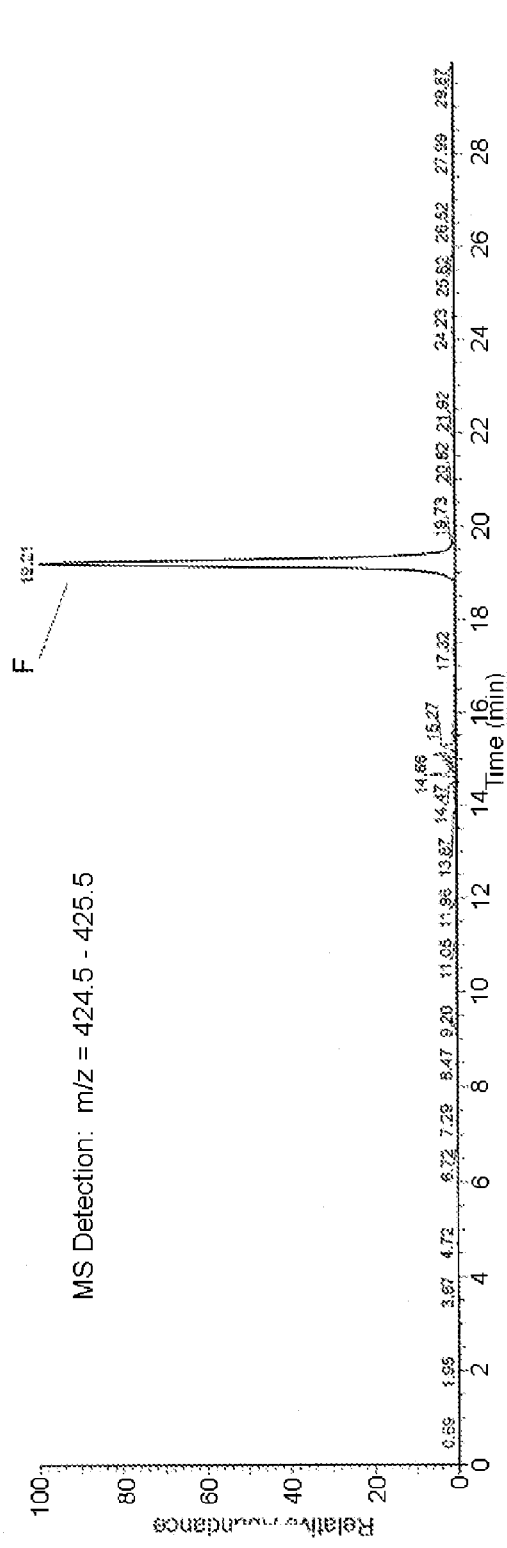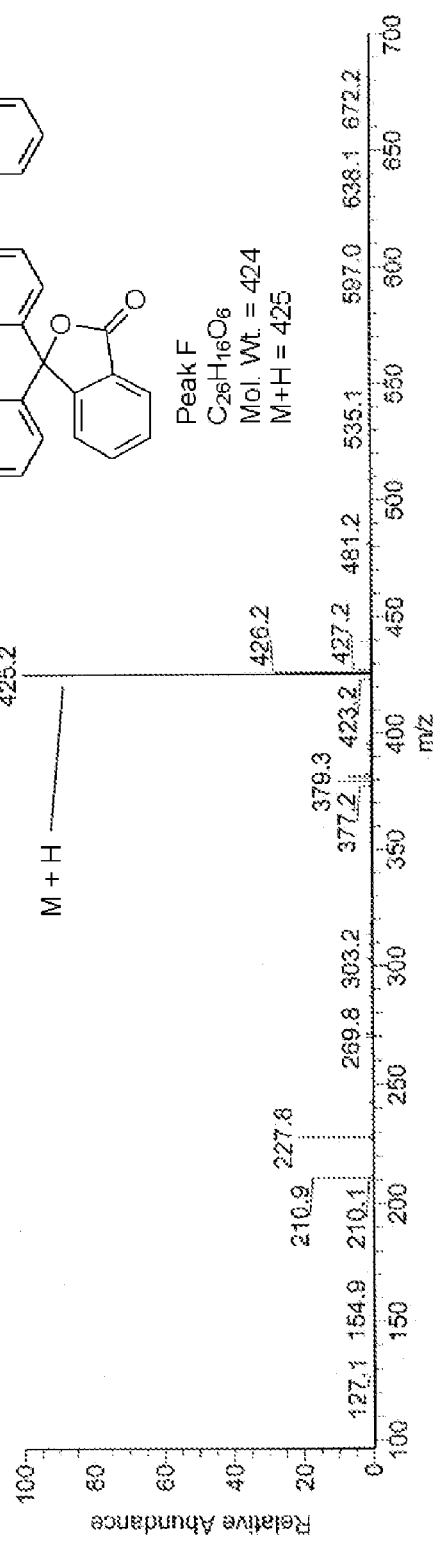
Fig. 16A
Fig. 16B
HPLC/MS of Impurity F in Fluorescein Drug Substance

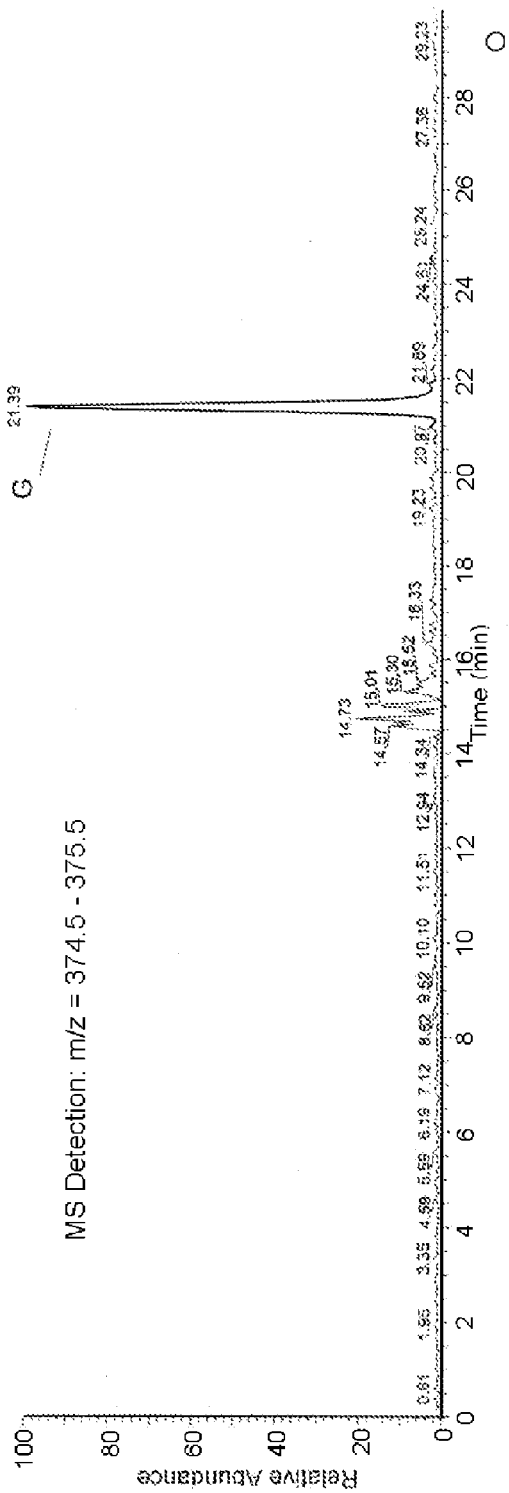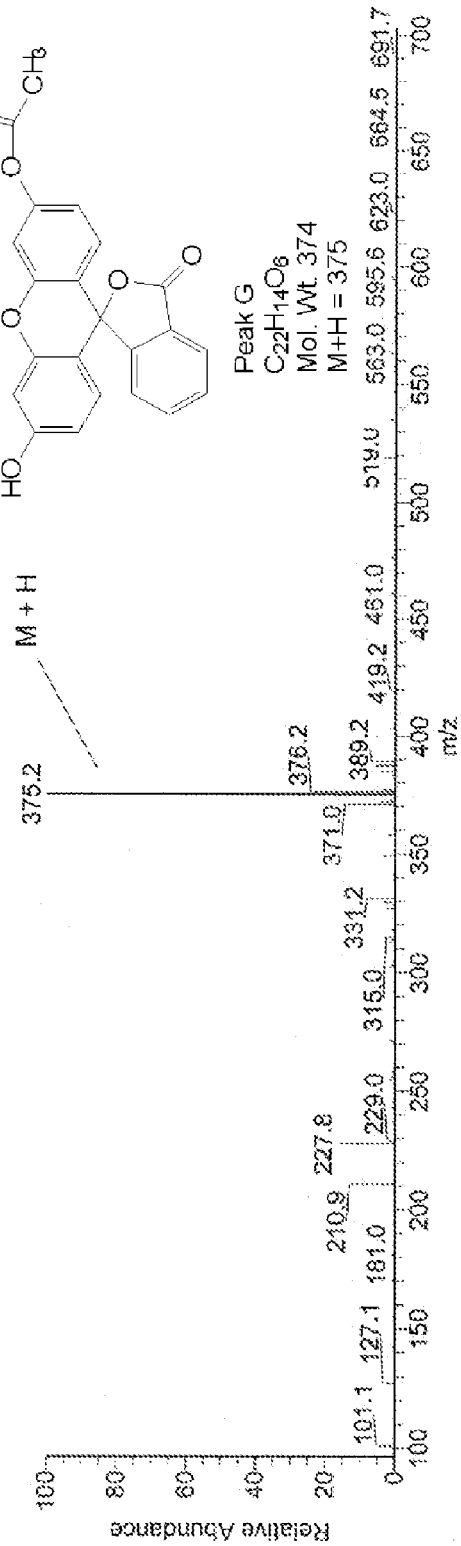
Fig. 17A HPLC/MS of Impurity G in Fluorescein Drug Substance
Fig. 17B Peak G, C22H14O6, Mol. Wt. 374, M+H = 375

HPLC/MS of Impurity H-1 in Fluorescein Drug Substance

HPLC/MS of Impurity H-2 in Fluorescein Drug Substance

UV-Vis Absorbance Scan of Impurity H-2

SUBSTANTIALLY PURE FLUORESCEIN

The present application claims benefit of U.S. Provisional Application Ser. No. 60/869,488, filed Dec. 11, 2006, which is hereby incorporated by reference for all purposes.

FIELD OF THE INVENTION

The present invention is directed to compositions comprising substantially pure fluorescein, processes for preparing substantially pure fluorescein, substantially pure fluorescein prepared by such processes, analytical methods for determining the purity of fluorescein, and a pharmaceutical compositions for use in angiography.

BACKGROUND OF THE INVENTION

Fluorescein is an orange-red compound, $C_{20}H_{12}O_5$, that exhibits intense fluorescence in alkaline solution and is used in applications such as medicine for diagnostic purposes, in oceanography as a tracer, and as a textile dye.

Fluorescein was first synthesized by German chemist Adolf Von Baeyer in 1871, from the petroleum derivatives resorcinol (1,3-dihydroxybenzene) and phthalic anhydride. Paul Erlich, a German bacteriologist, employed the fluorescent dye (as sodium salt fluorescein), then known as "uranin", to track the pathway of secretion of aqueous humor in the eye. This is said to be the first instance of fluorescent dye use in vivo to study physiology.

Fluorescein angiography is an important diagnostic tool that permits study of the condition of the blood vessels of the back of the eye. These vessels are a factor in many diseases that involve the retina. Angiography is performed by injecting fluorescein into a vein in the subject's arm. Within a short time (i.e., typically from a few to several seconds), the dye travels to the vessels in the back of the eye, and a camera with special filters is employed to image the dye as it circulates in the ocular blood vessels. Through examination of the images so produced, an assessment can be made about any circulation problems, for example, vessel leakage, swelling, abnormal or new vessels, and so on.

Fluorescein absorbs blue light, with peak absorption and excitation occurring at wavelengths between 465-490 nm. Fluorescence occurs at the yellow-green wavelengths of 520-530 nm. Although commonly referred to as fluorescein, the dye used in angiography is fluorescein sodium, the soluble disodium salt of fluorescein.

The normal adult dosage of fluorescein is 500 mg injected intravenously. It is typically packaged in doses of 5 mL of a 10% solution or 2 mL of a 25% solution. Upon entering the circulatory system, approximately 80% of the dye molecules bind to serum protein. The remaining unbound or free fluorescein molecules fluoresce when excited with light of the appropriate wavelength. The dye is metabolized by the liver to form fluorescein monoglucuronide, and is ultimately eliminated through the urine within 24 to 36 hours subsequent to administration.

It has been reported that the purity of fluorescein in fluorescein formulations may be correlated to side effects and tolerance to injection. ("Effective differences in the formulation of intravenous fluorescein and related side effects" by Yannuzi et al. in Am. J. Ophthalmol. 1974, 78 (2) pages 217-221). The elimination of all or substantially all impurities from fluorescein compositions utilized for angiography is therefore a primary objective of the present invention.

The following publications may be referred to for additional information regarding fluorescein compositions and processes for preparing and purifying fluorescein.

German Patent No. 136498 (Friedrich et al.) entitled "Process for Preparing Highly Purified Fluorescein for Injection Purposes" describes a process for preparing fluorescein using pyridine.

U.S. Patent Application Publication No. US2006/0106234A1 (Tran-Guyon et al.), entitled "High Purity Phthalein Derivatives and Method for Preparing Same", describes a process for preparing fluorescein using an anhydrous solvent.

The following patents or publications may also be consulted for further background: U.S. Pat. No. 5,637,733 (Sujeeth), entitled "Synthesis of Fluorescein Compounds with Excess Resorcinol as a Solvent" and U.S. Pat. No. 1,965,842 (Kranz) entitled "Production of Hydroxybenzene-Phthaleins".

Highly purified fluorescein is necessary for the preparation of solutions for injection purposes. The purified fluorescein used should ideally be: (i) free from impurities, which may be toxic and/or lack fluorescence; (ii) low in salt, which can lead to an unacceptably high osmolality or hypertonicity of the injectable fluorescein product; and (iii) low in color. Certain impurities are strongly colored. Absence of color at particular frequencies may therefore indicate the absence of such impurities. The color profile of fluorescein compositions is therefore considered a significant quality attribute and a visual marker of purity.

A method is needed to identify and quantify very low levels of impurities that may be present in fluorescein compositions. Such a method should be able to separate, identify, and quantify those impurities which may be present.

Thus, there is a need for a fluorescein composition that is highly pure, low in color, low in sodium chloride content and a process to produce such fluorescein that does not require the use of pyridine or other non-aqueous (and potentially noxious) solvent, as well as a method for determining the purity of such fluorescein. The present invention is directed to satisfying this need.

SUMMARY OF THE INVENTION

The present invention is directed to compositions comprising substantially pure fluorescein, to new and improved processes for the preparation of purified fluorescein, and to compositions of fluorescein produced via these processes. The present invention is also directed to a pharmaceutical composition for use in angiography comprising substantially pure fluorescein, and to a method of determining the purity of a fluorescein composition. The highly purified fluorescein produced by the method of the invention has a lower level of related-substance impurities than prior fluorescein compositions. The fluorescein produced by these new processes is also lower in color (at 590 nm) than other known compositions, providing a plainly visible maker for purity. The fluorescein of the present invention is also lower in sodium chloride content and therefore more easily formulated for pharmaceutical use than other known compositions. The processes of the invention improve on other known processes by eliminating the use of pyridine in the purification process, by not requiring the use of anhydrous solvent, by reducing the amount of acetic anhydride required to acetylate the crude fluorescein, and by improving the yield of highly purified fluorescein. The present invention also advances the state of the art by providing a reliable method for separating and quantifying related-substance impurities in fluorescein compositions, and for therefore determining the purity of fluorescein compositions.

The present invention may be embodied in various applications, including (without limitation) those summarized below:

One embodiment of the invention is directed to a composition comprising substantially pure fluorescein; more particularly, fluorescein that is substantially free of pyridine.

Another embodiment of the invention is directed to substantially pure fluorescein that does not contain any related-substance impurity at a concentration of greater than about 0.1% by weight; more preferably, 0.01% by weight.

Another embodiment of the invention is directed to substantially pure fluorescein having a color number of from about 0.015 to about 0.050 AUC.

Another embodiment of the invention is directed to substantially pure fluorescein having a residual chloride content of less than about 0.25% by weight.

Another embodiment of the invention is directed to substantially pure fluorescein where the total amount of substance-related impurities is less than about 0.6% by weight; preferably, less than 0.06% by weight.

Another embodiment of the present invention is directed to a process for preparing substantially pure fluorescein. The process comprises hydrolyzing diacetylfluorescein to form fluorescein, treating the fluorescein with charcoal, filtering, adding ethanol to the filtrate, adjusting the pH using an acidic solution to form a precipitate, filtering, and washing. In one aspect of this embodiment, the pH level is adjusted from about 1.0 to about 2.5. In other aspects, a cooling temperature is maintained of from about 20° C. to about 25° C. while adjusting the pH level, and the pH level is adjusted during a period of about 2 to 4 hours. The invention is also directed to substantially pure fluorescein compositions produced by such processes.

Another embodiment of the invention provides an HPLC method for quantifying the levels of fluorescein related-substance impurities. The method comprises obtaining a high-pressure liquid chromatogram of the composition; identifying peaks in the chromatogram corresponding to related-substance impurities and taking area measurements of the peaks to determine a relative concentration thereof. In one aspect of this embodiment, the peaks have relative HPLC retention times of about 0.75, 1.19, 1.23, 1.68 and 1.71. Another embodiment provides an HPLC/MS method for identifying related-substance impurities in fluorescein.

A preferred embodiment of the invention is directed to a pharmaceutical composition for use in angiography comprising substantially pure fluorescein; more particularly, a composition wherein the fluorescein is substantially free of pyridine.

Another preferred embodiment of the invention is directed to a pharmaceutical composition for use in angiography comprising substantially pure fluorescein wherein the composition does not contain any substance-related impurity at a concentration of greater than about 0.1% by weight; more preferably, 0.01% by weight.

Another preferred embodiment of the invention is directed to a pharmaceutical composition for use in angiography comprising substantially pure fluorescein wherein the total amount of related-substance impurities present in the composition is less than about 0.6% by weight; more preferably, less than about 0.06% by weight.

Another preferred embodiment of the invention is directed to a pharmaceutical composition for use in angiography comprising substantially pure fluorescein wherein the fluorescein has a color number of from about 0.015 to about 0.050 AUC.

Another preferred embodiment of the invention is directed to a pharmaceutical composition of fluorescein for use in angiography wherein the composition has a residual chloride amount of less than about 0.25% by weight.

The present invention is more fully discussed with the aid of the following figures and detailed description.

DETAILED DESCRIPTION OF THE INVENTION

Figure 1:
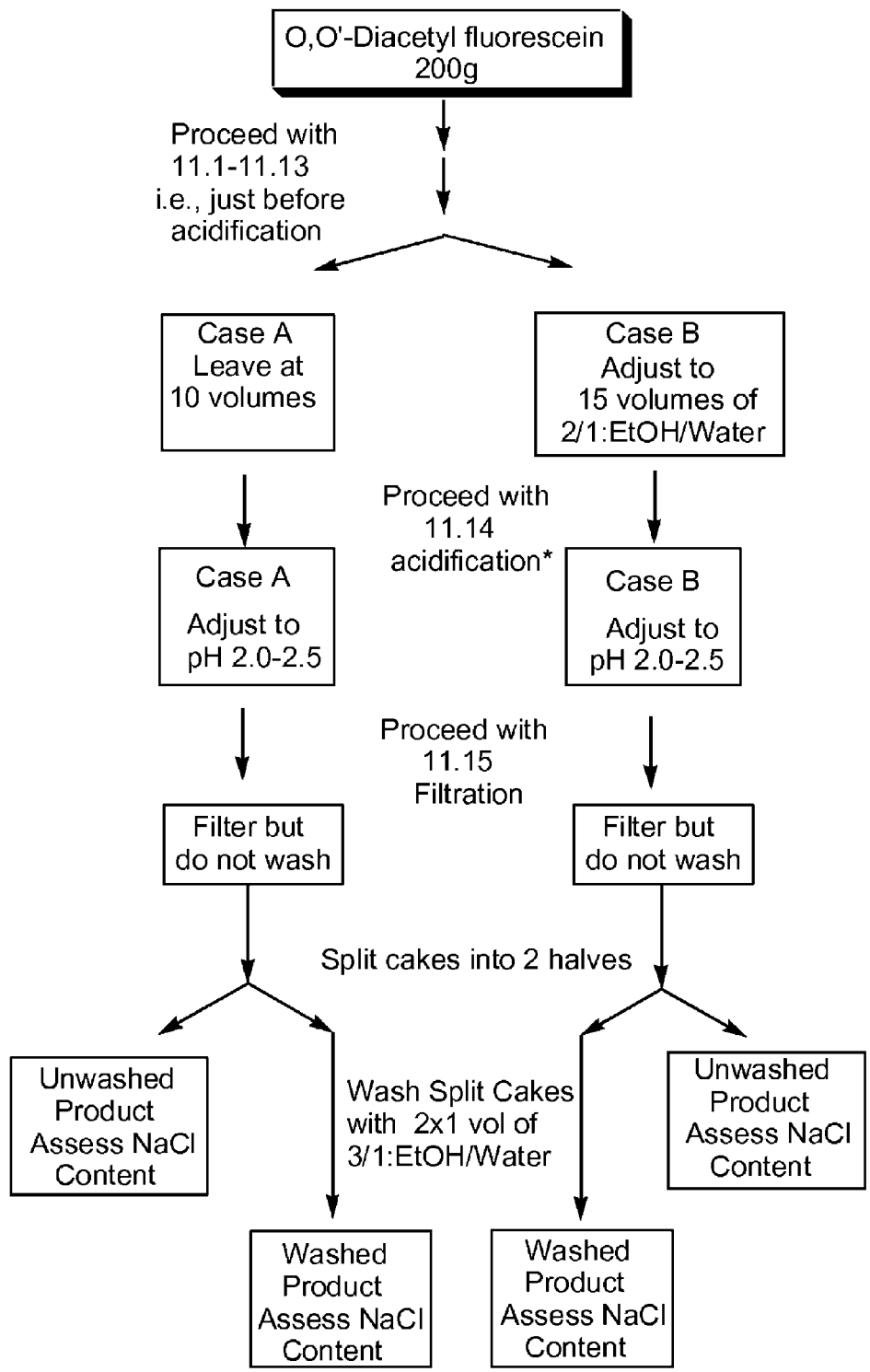
FIG. 1 is a schema of an experimental design for fluorescein washing experiments.

As utilized herein, the following abbreviations and terms, unless otherwise indicated, shall be understood to have the following meanings:

The abbreviation "APCI" means atmospheric pressure chemical ionization.

The abbreviation "M/S" or "MS" means mass spectrometer.

The abbreviation "HPLC" means high performance liquid chromatography.

The abbreviation "UV-Vis" means ultra violet visible.

The abbreviation "LC/MS" means liquid chromatography/mass spectrometer.

The term "charcoal" encompasses activated carbon agents that are effective at reducing color number. Exemplary agents include, but are not limited to, Norit® SA Plus and Norit® SX Ultra, commercially available from supplier Univar USA, Dallas, Tex. Forms of charcoal capable of reducing color number can be determined through routine experimentation. (It has been determined, for example, that another commercially available form of charcoal is not effective in reducing the color number, i.e., Darco® KB.)

The term "color number" is the absorbance of a 1.0% solution of fluorescein raw material prepared in an aqueous sodium hydroxide and sodium bicarbonate solution at pH 9.4, when measured at 590 nm.

The terms "fluorescein drug substance" and "fluorescein raw material" are used interchangeably herein.

The term "related-substance impurity" encompasses synthetic impurities, isomers, oxidation products, dimerization products and decomposition products of fluorescein and/or fluorescein reactants. Exemplary structures of such related-substance impurities are shown in FIG. 8.

The term "substantially free of pyridine" means that the fluorescein composition is at least 99% free of pyridine. More preferred is where the analytical purity is at least 99.9%; even further preferred is where the fluorescein composition is completely free of pyridine.

The term "substantially pure fluorescein" refers to the total absence, or near total absence, of impurities, such as related-substance impurities. For example, when a fluorescein composition is said to be substantially pure, there are either no detectable related-substance impurities, or if a single related-substance impurity is detected, it is present in an amount no greater than 0.1% by weight, or if multiple related-substance impurities are detected, they are present in aggregate in an amount no greater than 0.6% by weight The processes of the present invention produce fluorescein products with low related-substance impurity profiles. It is generally known that even purified fluorescein material may contain low levels of certain impurities, for example, resorcinol and 2-(2',4'-dihydroxybenzoyl)benzoic acid. However, it was not previously known that commercial samples of fluorescein may contain a number of impurities in addition to resorcinol and 2-(2',4'-dihydroxybenzoyl)benzoic acid. The amount of these potential impurities is reduced substantially via the processes of the present invention. Such impurities are collectively referred to herein as "related-substance impurities".

Figure 8:
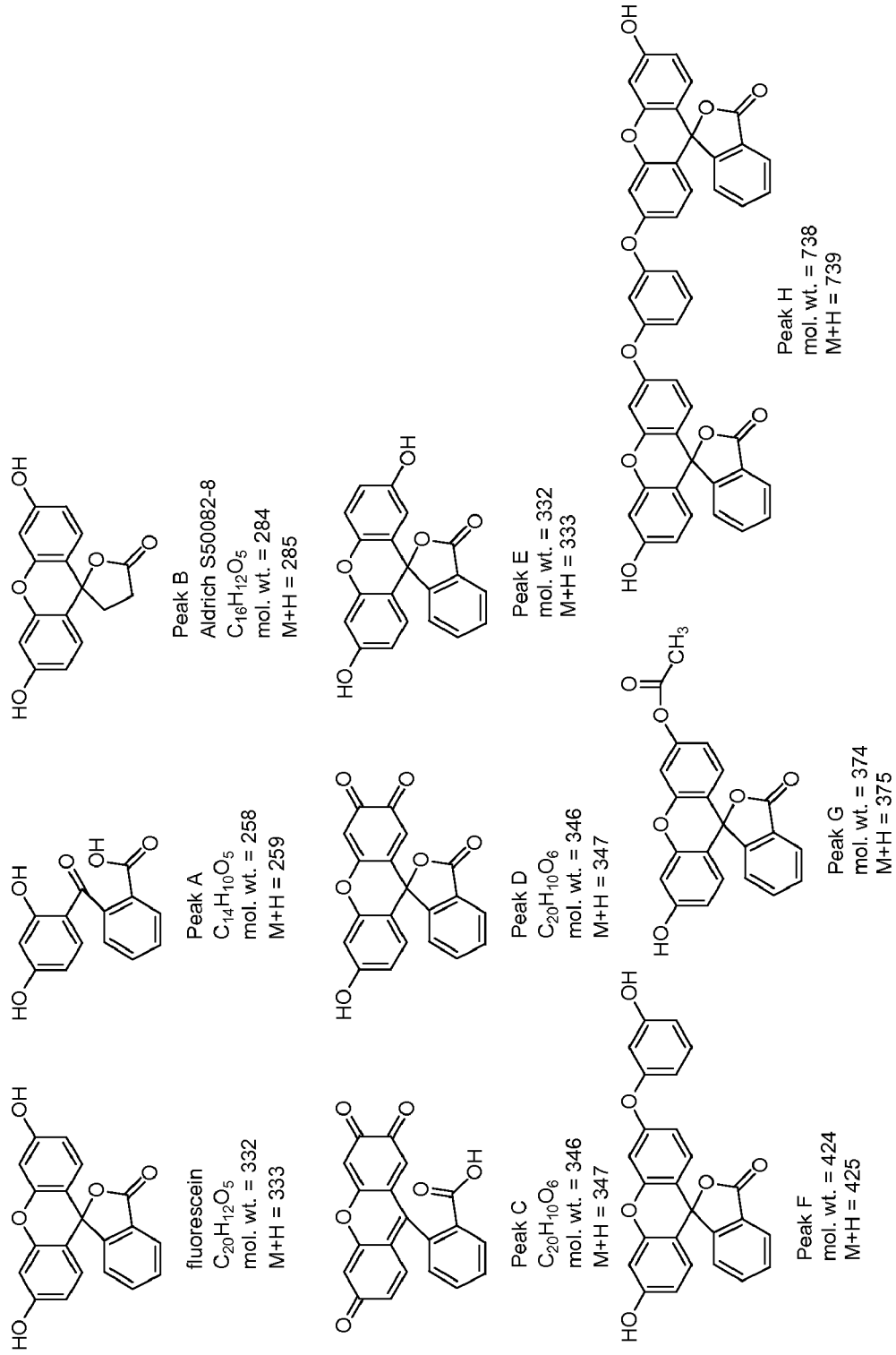
FIG. 8 is a diagram of the Structure of Fluorescein and Proposed Structures of Related-Substance Impurities, as described in Examples 5 and 6.

Experiments were conducted to determine the molecular weights of these related-substance impurities by LC/MS, and, although not desiring to be bound by theory, structures for these impurities are proposed herein (see FIG. 8). A process to resolve and quantify the low level of related-substance impurities which may be present even in purified fluorescein compositions was discovered and is described in detail below. It was discovered that the processes of the present invention provide a highly purified fluorescein that has substantially reduced levels of related-substance impurities. This can be seen in the impurity profiles of purified fluorescein drug substance of the present invention, as shown below in Table 1, compared to the impurity profile of technical grade fluorescein from various manufacturers, as shown in Table 2 below, and the impurity profile of fluorescein drug substance from various manufacturers as shown below in Tables 3 through 5.

TABLE 1

Impurity Profiles of Validation Batches of the Present Inventive Method Fluorescein Drug Substance[a]

| Reference No. | Impurity A | RRT 1.10 | Impurity C | Impurity D | Impurity E | Impurity F | Impurity G | Impurity H-1 | Impurity H-2 | RRT 1.74 | Total (%) |
|---|---|---|---|---|---|---|---|---|---|---|---|
| 1 | ND[b] | ND | ND | ND | ND | ND | ND | ND | ND | ND | 0.0 |
| 2 | ND | ND | ND | ND | ND | <LOQ[c] | ND | <LOQ[c] | <LOQ[c] | ND | 0.0 |
| 3 | ND | ND | ND | ND | ND | ND | ND | ND | <LOQ[c] | ND | 0.0 |

[a]Resorcinol was analyzed by a separate method in each of the three lots. The resorcinol concentration in each lot was less than 0.05%.
[b]ND = Not detected, <0.01%.[c]
[c]LOQ = Less than limit of quantitation of 0.025%; estimated at 0.01%.

TABLE 2

Impurity Profiles of Technical Grade Fluorescein from Various Manufacturers

| Supplier Reference No. | Impurity A (%) | RRT 1.10 (%) | Impurity C (%) | Impurity D (%) | Impurity E (%) | Impurity F (%) | Impurity G (%) | Impurity H-1 (%) | Impurity H-2 (%) | RRT 1.74 (%) | Total (%) |
|---|---|---|---|---|---|---|---|---|---|---|---|
| Supplier B 4 | 0.3 | — | — | 0.1 | — | 0.7 | — | 0.3 | 0.3 | — | 4.4[a] |
| Supplier B 5 | 0.4 | — | — | 0.06 | — | 0.6 | — | 0.2 | 0.2 | — | 3.8[a] |

TABLE 2-continued

Impurity Profiles of Technical Grade Fluorescein from Various Manufacturers

| Supplier Reference No. | Impurity A (%) | RRT 1.10 (%) | Impurity C (%) | Impurity D (%) | Impurity E (%) | Impurity F (%) | Impurity G (%) | Impurity H-1 (%) | Impurity H-2 (%) | RRT 1.74 (%) | Total (%) |
|---|---|---|---|---|---|---|---|---|---|---|---|
| Supplier B 6 | 0.2 | — | — | 0.01 | — | 0.5 | — | 0.2 | 0.2 | — | 1.5[a] |
| Supplier B 7 | 0.6 | — | — | 0.07 | — | 0.07 | — | 0.06 | 0.1 | — | 0.9 |
| Supplier B 8 | 0.7 | — | — | 0.07 | — | 0.08 | — | 0.06 | 0.1 | — | 1.0 |
| Supplier B 9 | 0.6 | — | — | 0.7 | — | 0.7 | — | 0.4 | 0.1 | — | 0.9 |
| Supplier B 10 | 0.45 | — | — | 0.59 | — | 0.15 | — | 0.21 | 0.22 | — | 4.21[b] |
| Supplier B 11 | 0.64 | — | — | 0.53 | — | 0.14 | — | 0.18 | 0.19 | — | 4.15[b] |
| Supplier C 12 | 0.68 | — | — | 0.54 | — | 0.14 | — | 0.18 | 0.19 | — | 4.20[b] |
| Supplier C 13 | — | — | — | 1.22 | — | 0.11 | — | 0.97 | 0.98 | 0.11 | 5.57[c] |
| Supplier D 14 | 5.9 | — | — | 0.2 | — | 0.8 | — | 0.01 | 0.01 | — | 9.4[d] |
| Supplier D 15 | 5.6 | — | — | 0.1 | — | 0.9 | — | 0.01 | 0.02 | — | 9.6[d] |
| Supplier D 16 | 5.3 | — | — | 0.2 | — | 1.0 | — | 0.01 | 0.02 | — | 9.5[d] |
| Supplier D 17 | 5.3 | — | — | 0.2 | — | 1.0 | — | 0.01 | 0.03 | — | 9.7%[d] |

[a]Unknown impurities also present ranging in concentration from 0.06% to 0.9%.
[b]Unknown impurities also present ranging in concentration from 0.06% to 0.7%.
[c]Unknown impurities also present ranging in concentration from 0.05% to 0.5%.
[d]Unknown impurities also present ranging in concentration from 0.06% to 0.8%.

TABLE 3

Impurity Profile of Fluorescein Drug Substance Manufactured by Supplier A

| Supplier Reference No. | Impurity A (%) | RRT 1.10 (%) | Impurity C (%) | Impurity D (%) | Impurity E (%) | Impurity F (%) | Impurity G (%) | Impurity H-1 (%) | Impurity H-2 (%) | RRT 1.74 (%) | Total (%) |
|---|---|---|---|---|---|---|---|---|---|---|---|
| Supplier A 18 | <0.05 | — | — | — | 0.1 | 0.3 | — | — | — | — | 0.4 |
| Supplier A 19 | <0.05 | — | — | — | <0.05 | 0.09 | — | — | — | — | 0.09 |
| Supplier A 20 | 0.2 | — | — | — | 0.06 | 0.09 | — | — | — | — | 0.4 |

TABLE 4

Impurity Profile of Fluorescein Drug Substance Manufactured by Supplier E

| Supplier Reference No. | Impurity A (%) | RRT 1.10 (%) | Impurity C (%) | Impurity D (%) | Impurity E (%) | Impurity F (%) | Impurity G (%) | Impurity H-1 (%) | Impurity H-2 (%) | RRT 1.74 (%) | Total (%) |
|---|---|---|---|---|---|---|---|---|---|---|---|
| Supplier E 21 | <0.05 | — | <0.05 | — | <0.05 | <0.05 | 0.08 | — | — | — | 0.08 |
| Supplier E 22 | <0.05 | — | <0.05 | — | <0.05 | <0.05 | 0.07 | — | — | — | 0.07 |
| Supplier E 23 | <0.05 | — | <0.05 | — | <0.05 | <0.05 | 0.1 | — | — | — | 0.1 |
| Supplier E 24 | — | — | — | <0.05 | — | <0.05 | — | 0.06 | <0.05 | — | 0.06 |
| Supplier E 25 | 0.07 | — | — | 0.05 | — | 0.2 | <0.05 | 0.1 | 0.2 | — | 0.6 |
| Supplier E 26 | 0.06 | — | — | 0.05 | — | 0.2 | <0.05 | 0.1 | 0.2 | — | 0.6 |
| Supplier E 27 | 0.07 | — | — | 0.05 | — | 0.2 | <0.05 | 0.1 | 0.2 | — | 0.6 |

TABLE 5

Impurity Profile of Fluorescein Drug Substance Manufactured by Supplier F

| Supplier and Reference No. | Impurity A (%) | RRT 1.10 (%) | Impurity C (%) | Impurity D (%) | Impurity E (%) | Impurity F (%) | Impurity G (%) | Impurity H-1 (%) | Impurity H-2 (%) | RRT 1.74 (%) | Total (%) |
|---|---|---|---|---|---|---|---|---|---|---|---|
| Supplier F 28 | 0.1 | 0.03 | — | 0.05 | — | 0.2 | — | 0.1 | 0.1 | 0.03 | 0.7 |
| Supplier F 29 | 0.03 | <0.025 | — | 0.03 | — | 0.05 | — | 0.05 | 0.06 | <0.025 | 0.2 |
| Supplier F 30 | 0.05 | <0.025 | — | 0.04 | — | 0.1 | — | 0.1 | 0.1 | 0.04 | 0.5 |
| Supplier F 31 | 0.04 | <0.025 | — | 0.04 | — | 0.07 | — | 0.09 | 0.1 | 0.03 | 0.4 |
| Supplier F 32 | 0.04 | — | — | 0.04 | — | 0.1 | — | 0.07 | 0.08 | — | 0.3 |
| Supplier F 33 | 0.03 | — | — | 0.04 | — | 0.09 | — | 0.07 | 0.07 | — | 0.3 |
| Supplier F 34 | 0.04 | — | — | 0.03 | — | 0.08 | — | 0.05 | 0.05 | — | 0.3 |
| Supplier F 35 | 0.03 | — | — | 0.04 | — | 0.08 | — | 0.07 | 0.08 | — | 0.3 |
| Supplier F 36 | 0.03 | — | — | 0.04 | — | 0.1 | — | 0.08 | 0.1 | — | 0.4 |
| Supplier F 37 | 0.03 | — | — | 0.04 | — | 0.08 | — | 0.07 | 0.09 | — | 0.3 |
| Supplier F 38 | 0.03 | — | — | 0.04 | — | 0.1 | — | 0.08 | 0.07 | — | 0.3 |
| Supplier F 39 | 0.03 | — | — | 0.0 | — | 0.1 | — | 0.09 | 0.07 | — | 0.3 |
| Supplier F 40 | 0.03 | — | 0.03 | 0.04 | — | 0.08 | — | 0.08 | 0.07 | — | 0.3 |
| Supplier F 41 | 0.03 | — | 0.03 | 0.04 | — | 0.07 | — | 0.07 | 0.07 | — | 0.3 |
| Supplier F 32 | 0.03 | — | 0.03 | 0.04 | — | 0.09 | — | 0.07 | 0.07 | — | 0.3 |
| Supplier F 43 | 0.04 | — | — | 0.03 | — | 0.09 | — | 0.07 | 0.09 | — | 0.3 |

An outline of the general process involved in this invention is illustrated below. Commercial-grade fluorescein is diacetylated via reaction with acetic anhydride at reflux temperatures. The so-produced diacetylated fluorescein is isolated, and then reacted with base to produce the deacetylated fluorescein, which is then treated with charcoal to produce a low-color fluorescein of high purity and low chloride content. The reaction scheme is illustrated below:

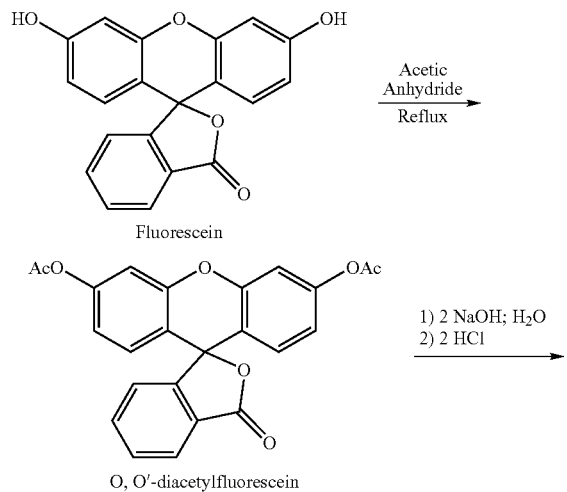

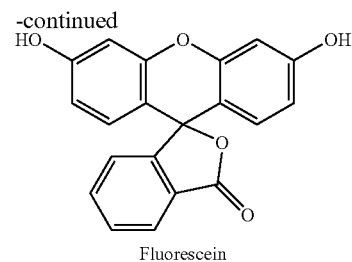

Fluorescein

The particular solvents, reaction times and temperatures, and pH values used to prepare the pure fluorescein of this invention have been determined based on a series of experiments. The goals of these experiments were to obtain a high purity pharmaceutical grade fluorescein of low color and salt content, and to avoid the use of a noxious solvent used in prior known methods, namely pyridine. Additional goals were to minimize the expense and time involved in the processes, by, for example, using the minimum amounts of solvents, or reducing the reaction cycle time(s) of the necessary steps.

The process of purifying fluorescein begins with converting fluorescein to O,O'-diacetylfluorescein. For this purpose acetic anhydride is used as both solvent and reagent, avoiding altogether the use of pyridine, a noxious solvent used in a prior art process. Thus, a mixture of fluorescein and acetic anhydride is stirred for several hours at reflux, and the resulting suspension is allowed to cool. Further cooling to freezing or just below effects full crystallization. The crystallized material is collected and washed first with cold acetic anhydride and then with cold acetone. The material is then resuspended in acetone with stirring and gentle heat. After cooling, the white crystalline material is collected, washed with cold acetone, and air dried, to provide high purity O,O'-diacetylfluorescein.

Next, the O,O'-diacetylfluorescein is converted back to fluorescein, with the formation of the sodium salt and removal of final impurities. To effect this conversion, the acetyl groups of O,O'-diacetylfluorescein are hydrolyzed using a caustic solution. Thus, O,O'-diacetylfluorescein and methanol are charged to a suitable vessel, a prepared solution of sodium hydroxide in deionized water is added, and the mixture is heated to reflux with agitation. The mixture is then cooled, filtered using a filter aid, and then washed with methanol. The volume of the filtrate is then reduced by vacuum distillation, water is added, and the reaction mixture is cooled. The pH of the reaction mixture is then adjusted to between 8.5 and 8.7. A suitable charcoal, for example, Norit® SX Ultra is added with agitation for one hour. If necessary, the charcoaling step is repeated. Next follow the critical precipitation steps. First, ethanol is added to the filtrate so that a 2:1 proportion of ethanol to water is obtained. This proportion is based upon the unexpected discovery that a higher proportion of organic solvent to water in the precipitation procedure yields a lower chloride content in the fluorescein product. The experiments conducted to discern this effect are described further below. Next, to acidify the fluorescein, a diluted hydrochloric acid solution is added so that a calibrated pH range is established. This range is based upon the unexpected discovery that a lower pH provides a product with a more desirable color. More specifically, it was determined through experimentation that the optimum pH range of the filtrate should be between 1.0 and 2.5, and that the acidification should be conducted slowly, for example, over a time period of two to four hours, so as to avoid aggregation of the product, and with cooling. After further agitation and cooling, the fluorescein is then isolated by filtration. The product is washed with a solution of water and ethanol, and the product dried to provide an 80-90% yield of very high quality fluorescein. The high-purity fluorescein may be used in the preparation of fluorescein for injection. For this purpose, the fluorescein is converted to the soluble disodium salt form using sodium hydroxide, and filled into ampoules for subsequent sterilization.

One example of the experimentation conducted to achieve the process of the invention is the calibration of the pH range at which the fluorescein product is precipitated. This pH range was adjusted from a higher to a lower range based in part on empirical observations regarding the color spectrum of the product formed. Thus, it was determined that the optimal pH range at which the fluorescein product should be precipitated in order to achieve the goal of a low color product is from about pH 1.0 to about pH 2.5.

It was also unexpectedly discovered that higher proportions of organic solvent to aqueous solvent, in the precipitation procedure, yield a lower chloride content in the fluorescein product. This result was not anticipated, as it was expected that a low organic/aqueous ratio would have been necessary to reduce the sodium chloride level. The use of higher proportions of organic solvent has an added benefit of improving the filtration rate, thereby reducing the time required to process the material.

Figure 2:
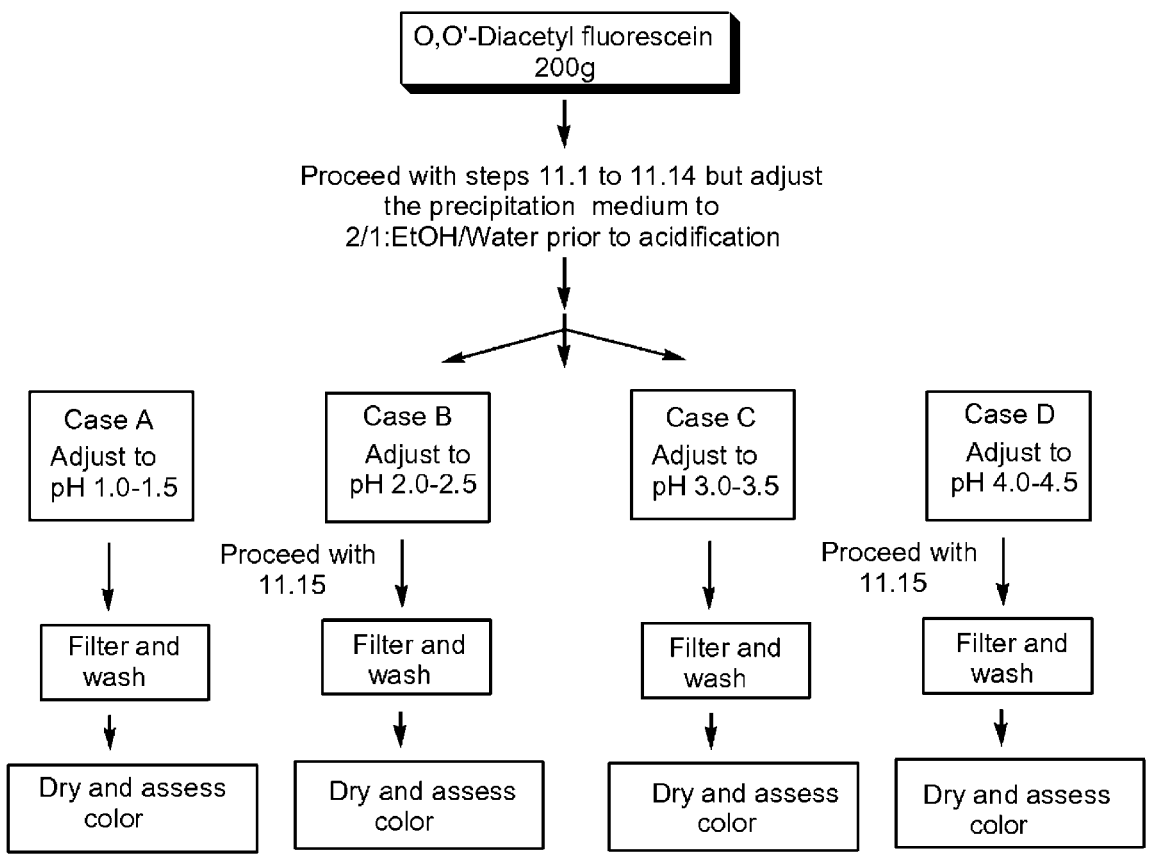
FIG. 2 is a schema of an experimental design for fluorescein pH/precipitation experiments.

Further precipitation experiments were conducted to develop processes for the present invention and are described below, and shown in FIGS. 1 and 2. In particular, experiments were conducted to reduce the chloride level by changing the precipitation process, as shown in Table 6 below.

TABLE 6

Precipitation Experiments

| Experiment Reference | Ratio of Water:Ethanol | Volumes | Washed* (Y or N) | Chloride (% wt) | Comment |
|---|---|---|---|---|---|
| A | 1:1 | 10 | N | 0.91 | Yellow-red solid |
|   | 1:1 | 15 | N | 0.87 | Yellow-red solid |
| B | 1:1 | 10 | N | 0.80 | Yellow-red solid |
|   | 2:1 | 15 | N | 0.97 | Yellow-red solid |
| C | 1:1 | 10 | N | 0.76 | Yellow-red solid |
|   | 1:2 | 15 | N | 0.65 | Dark red solid |
| D | 1:1 | 10 | N | 1.45 | 86% yield Yellow-red solid |
| E | 1:2 | 15 | N | 0.45 | 92% yield Dark red solid |
| F | 1:1 | 10 | Y | 0.10 | 87% yield Yellow-red solid |
| G | 1:2 | 15 | Y | 0.0056 | 78% yield Dark red solid |
| H | 1:1 | 10 | N | 1.05 | Yellow-red solid |
| I | 1:2 | 15 | N | 0.49 | Dark red solid |
| J | 1:1 | 10 | Y | 0.13 | Yellow-red solid |
| K | 1:2 | 15 | Y | 0.026 | Dark red solid |

*Water:Ethanol, 3:1, 2 × 1 volume wash

Table 6 shows that a change in the solvent ratio of the precipitation medium affects the amount of chloride present. In particular, increasing the ratio of ethanol to water in the precipitation medium produces a lower chloride content. Experiment A shows a marginal decrease in the chloride content when the volume of the water:ethanol (1:1) precipitation medium is increased from 10 volumes (reference) to 15 volumes (See Table 6). Experiment B compares the precipitation from water:ethanol (1:1, 10 volumes, reference) to precipitation from water:ethanol (2:1, 15 volumes). The result from the experiment is counter-intuitive in that the reference reaction having a lower water content and less volume produces a lower chloride content.

Experiment C compares the precipitation from water:ethanol (1:1, 10 volumes, reference) to precipitation from water:ethanol (1:2, 15 volumes). The results of Experiment C show that the higher organic content precipitation medium produces lower chloride content.

The trend that the higher organic content in the precipitation medium produces a lower chloride content is reproduced in Experiments D, E, F and G, and Experiments H, I, J and K for both the unwashed and the washed product. Although the results appear counter-intuitive, it is believed, without being bound by theory that the higher organic content allows for a faster and more efficient wash of the product cake.

Another aspect considered is whether fluorescein color is dependent upon the pH of the precipitation medium; see Table 7 below, wherein a precipitation medium of ethanol: water in a ratio of 2:1 is used.

TABLE 7

Fluorescein Color as a Function of pH
[Precipitation Medium of Ethanol:Water (2:1)]

| Experiment Reference | pH 1.0-1.5 | pH 2.0-2.5 | pH 3.0-3.5 | pH 4.0-4.5 |
|---|---|---|---|---|
| L | Red Solid | Red Solid | Maroon Solid | Brown Solid |

The results indicate that fluorescein color is sensitive to pH changes. For example, at a pH of about 3.0, the appearance of the product begins to take on a maroon hue, which is deemed to be undesirable.

Examples 1-8 below are provided to further illustrate certain embodiments of the invention. Representative data obtained from Examples 5, 6, 7 and/or 8 are shown in FIGS. 9 to 19.

The data for FIGS. 9-14 were obtained with an LC/MS using a thermospray mass spectrometer interfaced with an HPLC. Peaks were observed by use of a UV detector (280 nm) and a thermospray mass spectrometer. Experimental Conditions: Instrument=Vestec Model 201B Thermospray mass spectrometer interfaced to a Waters Model 600 MS HPLC system and a Waters Model 486MS UV detector (280 nm); Column=Waters Symmetry C-8, 5μ, 3.9×150 mm; Mobile Phase=Linear gradient programmed from 0% B to 100% B over 25 minutes; Mobile Phase A=0.1 M ammonium acetate in 10:90 V:V methanol:water; Mobile Phase B=0.1 M ammonium acetate in methanol; Flow rate=1.0 mL/minute; Sample concentration=Neat; and Injection Volume=20 μL.

The data for FIGS. 15-20 was obtained with an LC/MS using a mass spectrometer interfaced with an HPLC. The mass spectrometer was used with the atmospheric pressure chemical ionization (APCI) interface and the spectrometer was operated in the positive ion mode of detection. Peaks were observed by use of a UV-Vis detector monitoring the total absorbance from 220-500 nm and the mass spectrometer. A Waters Symmetry C-8 column (3.9×150 mm) was used at a flow rate of 0.6 mL/minute and was programmed from 0% mobile phase B to 100% mobile phase B over 30 minutes. Mobile phase B was 0.01 M ammonium acetate in methanol and mobile phase A was 0.01 M ammonium acetate in 10:90/methanol:water.

EXAMPLE 1

Formation of Fluorescein Diacetate

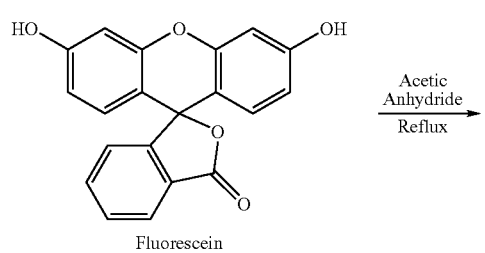

Fluorescein

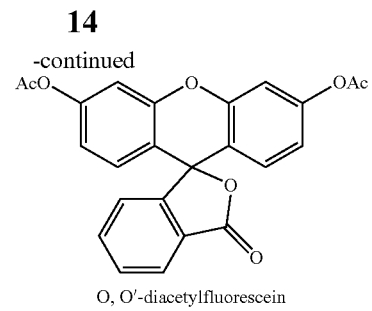

O, O'-diacetylfluorescein

To a 5 liter, 3 necked round bottom flask Fluorescein (1000 g, 3.01 mol) and acetic anhydride (1622 g, 15.9 mol) were added. The resulting mixture was stirred for 3-5 hours at reflux and the resulting suspension was allowed to cool to room temperature. With continuous stirring, the reaction mixture was further cooled to −5 to 3° C. to effect full crystallization. The crystallized material was collected on a Buchner filter, washed with cold acetic anhydride (2×500 mL) and then cold acetone (1×600 mL). The material was partially dried and re-suspended in acetone (1000 mL) with stirring and gentle heat. Once cooled, the white crystalline material was collected on a filter, washed with cold acetone (2×700 mL) and was air dried. Yield: ~75%-85%; Single spot via TLC; MP=203-205.5° C.; and Purity 99.7%.

EXAMPLE 2

Formation of Fluorescein from Diacetyl Fluorescein, Formation of Sodium Salt and Removing Final Impurities

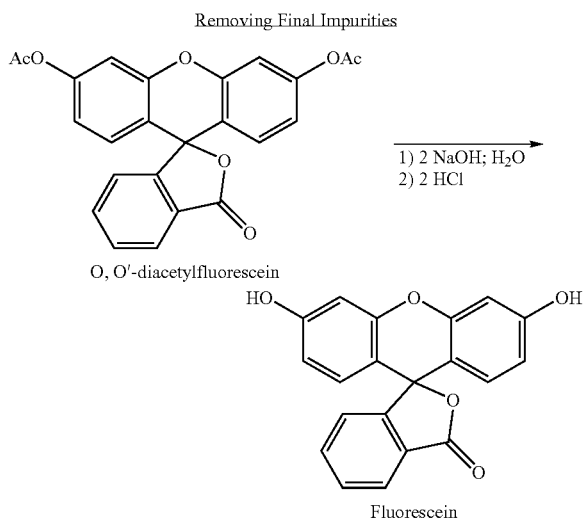

O,O'-diacetylfluorescein (1000 g) and methanol (4000 mL) were charged into a suitable reactor. Separately, a solution of sodium hydroxide solution (480 g, 50% caustic) was prepared in deionized water (620 mL). The sodium hydroxide solution was charged into the reactor containing the O,O'-diacetylfluorescein and methanol. The mixture was heated to reflux and agitated at reflux for 90 minutes. The reaction mixture was cooled to between 20° C. and 25° C. The mixture was filtered using filter aid (100 g) and followed by a wash with methanol (500 mL). The filtrate (5000 mL) was distilled under vacuum to a residual volume of between 1400 mL to 1700 mL and the reaction mixture was then cooled to between 20° C. and 25° C. Deionized water (5000 mL) was added to the distillation concentrate. Separately, a solution of sodium hydroxide solution (56 g, 50% caustic) was prepared in deionized water (72 g). The freshly prepared sodium hydroxide solution (100 mL) was used to adjust the pH of the reaction to between 8.5 and 8.7. Norit SX Ultra (100 g), filter aid (100 g) and deionized water (500 mL) were charged to the reaction at room temperature and the mixture was subsequently agitated for 1 hour. The batch was filtered and additional Norit SX Ultra (100 g) and deionized water (500 mL) was charged to the filtrate at room temperature and the mixture was subsequently agitated for 1 hour. The batch was filtered and was washed with deionized water (2000 mL). Ethanol (10000 mL) was charged to the filtrate. Separately a hydrochloric acid solution was prepared by dissolving muriatic acid (32%, 820 g) in deionized water (320 mL). The diluted acid solution was used to adjust the pH of the filtrate to between 1.0 and 2.5 while the temperature of the batch was maintained between 20° C. and 25° C. The batch was agitated between 20° C. and 25° C. for 1 hour and was then isolated by filtration. The cake was washed with a solution of (Water for Injection:Ethanol):(3:1), (2×1000 mL). The product was dried to give a typical 80-90% yield of very high quality fluorescein.

EXAMPLE 3

Fluorescein Drug Substance Color Intensity

Equipment

Spectrophotometer capable of accepting 1 cm cells and scanning from 660 nm to 570 nm.

Spectrophotometer cells (1 cm path length) of a material appropriate for wavelengths 660 nm to 570 nm, such as quartz.

The intensity of the color of fluorescein drug substance was measured, as described below. The procedure was used to determine the color of a 1.0% solution of fluorescein raw material prepared in an aqueous of sodium hydroxide and sodium bicarbonate solution at pH 9.4 by measuring its absorbance at 590 nm. This value may also be referred to as the "color number". An increase in the absorption measurement at 590 nm corresponds to an increase in the visible color intensity of the finished drug product.

Fluorescein (250 mg±5 mg, accurately weighed) and sodium bicarbonate (50 mg) were weighed into a 25 mL beaker. Sodium hydroxide (5 ml of 1%) was added. The solution was warmed gently while stirring. Sodium hydroxide (1%, up to 1 additional mL, a total of 6.0 mL) was added until all material was dissolved and the solution clear. The reaction was cooled to room temperature. The pH was adjusted the pH to 9.4, using 1% sodium hydroxide dropwise if necessary. If pH was above 9.4, the solution was discarded and re-prepared using less sodium hydroxide. The solution was quantitatively transferred to a volumetric flask (25 mL) and QS to 25.0 mL with purified water. The final concentration was 10 mg/mL, or 1%.

Method

Figure 3:
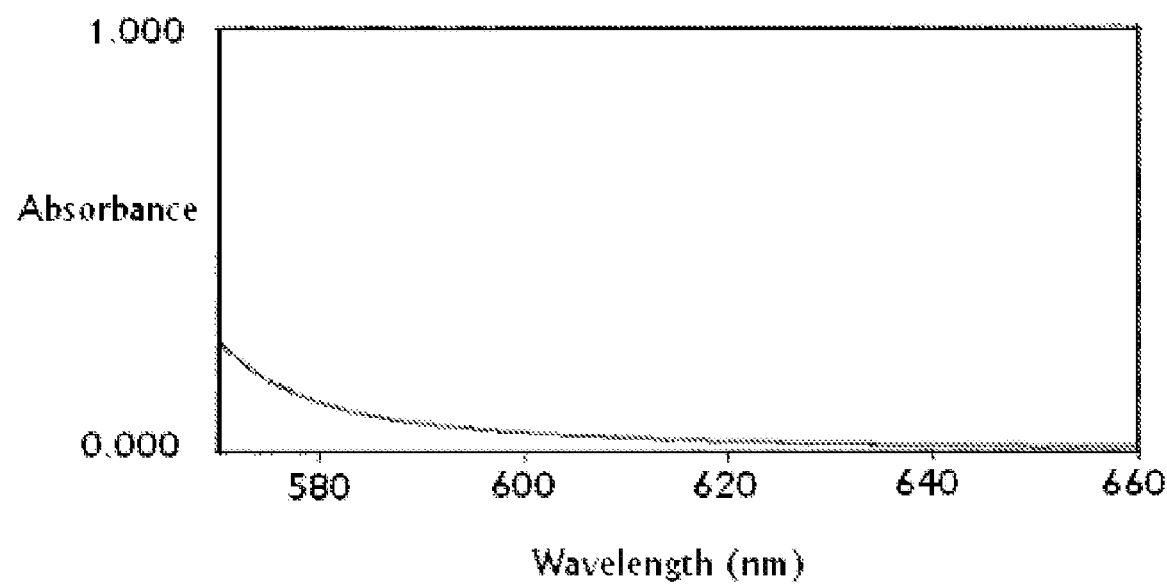
FIG. 3 is a UV/VIS Spectrum showing the color intensity of fluorescein drug substance as described in Example 3.
Figure 4:
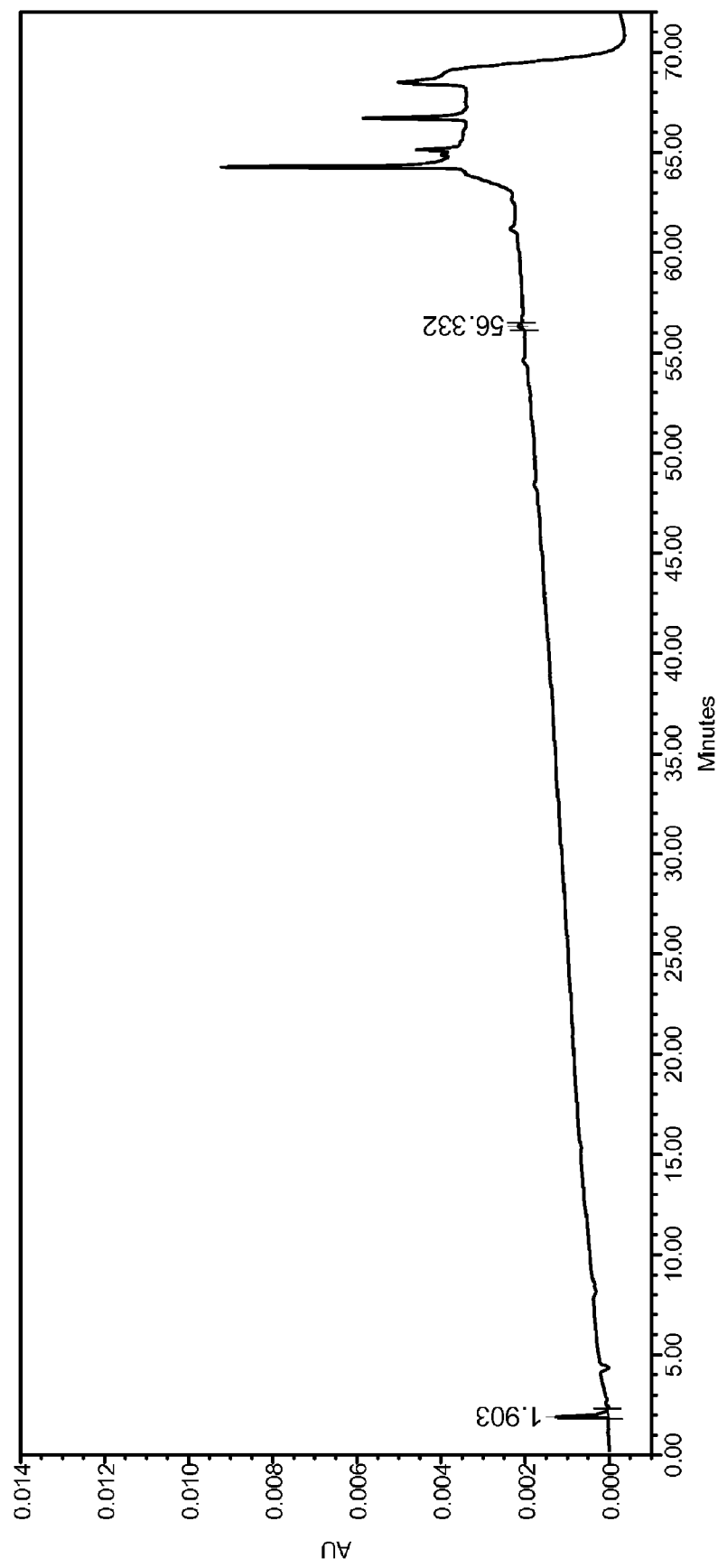
FIG. 4 is an HPLC chromatogram of diluent blank as described in Example 5.
Figure 5:
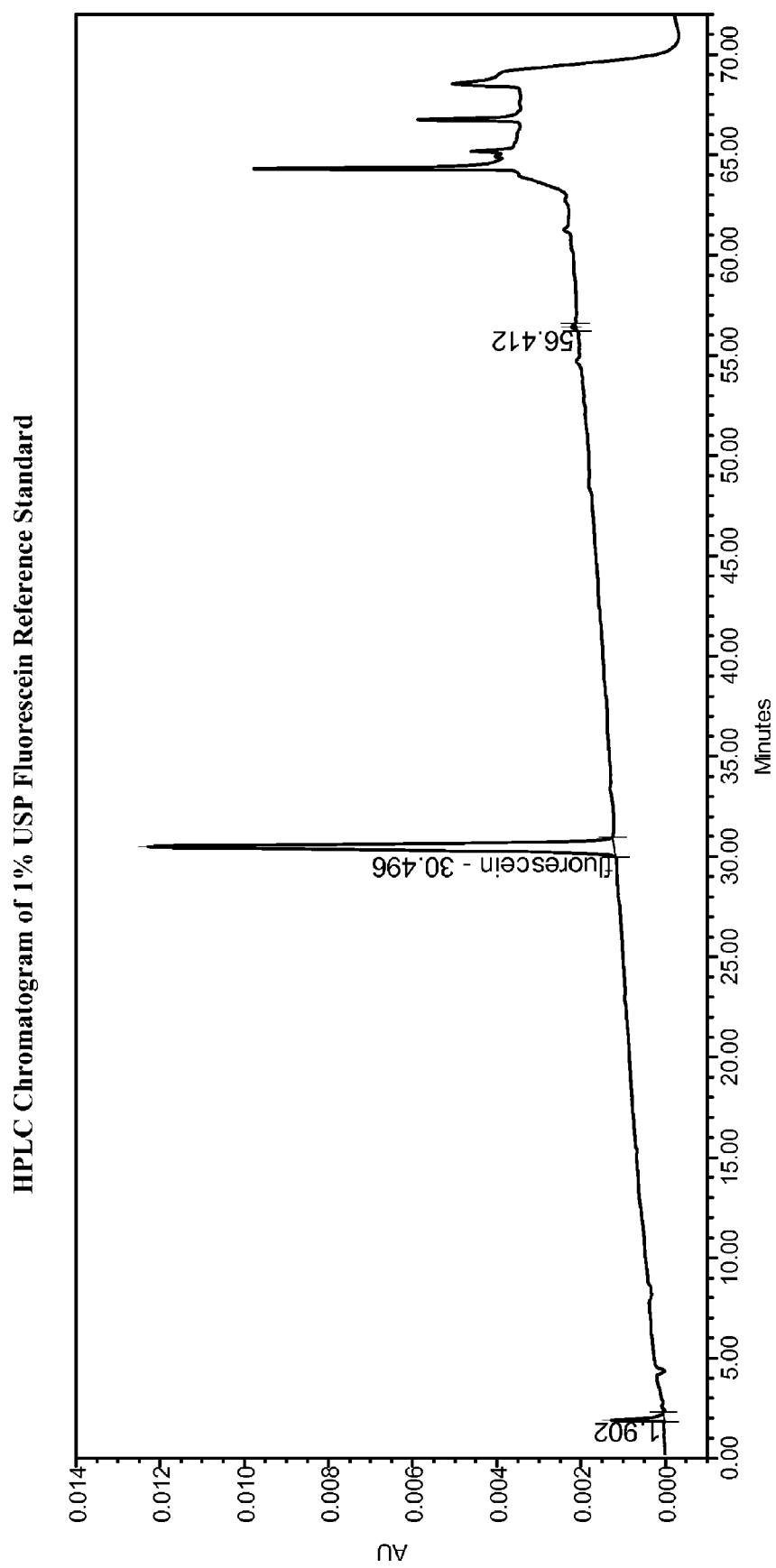
FIG. 5 is an HPLC chromatogram of 1% USP Fluorescein Reference Standard as described in Example 5.

The spectrophotometer was zeroed by establishing a blank user baseline with purified water in both the sample and reference cell cuvettes, scanning from 660 nm to 570 nm at a rate of 100 nm/min. Fluorescein solution (1%) was added to the sample cuvette. The sample solution was scanned from 660 nm to 570 nm, at a rate of 100 nm/min. The absorbance reading was recorded at 590 nm. A duplicate measurement was performed on a separate aliquot of sample. Table 1 lists typical color number results for several fluorescein raw material sample testing using this method. The results were corrected using the equation shown in Section below. FIG. 3 shows a typical spectrum obtained from a fluorescein raw material sample.

Calculations

The absorbance readings were corrected for sample concentration as follows:

$$Absorbance_{corrected} = Absorbance \times \frac{(Target\ Weight)}{(Actual\ Weight)}$$

Color intensity measurements on sample fluorescein lots were obtained as described in Example 2, and listed in Table 8 below.

TABLE 8

| Color Number for 1% Fluorescein Solutions | |
|---|---|
| Sample | Color Number |
| 1 | 0.028 A.U. |
| 2 | 0.032 A.U. |
| 3 | 0.018 A.U. |
| 4 | 0.025 A.U. |

EXAMPLE 4

Fluorescein Residual Chloride Determination Using Potentiometric Titration

Equipment
Brinkman 716 DMS Titrino Automated Titrator or equivalent
Brinkman 730 Sample Changer and 759 Swing Head Autosampler or equivalent
Ag Titrode electrode
5-Place analytical balance or equivalent
Sonicator
Hot plate
Centrifuge capable of 3,000 rpm
Culture tubes, 16×125 mm, VWR Cat #47729-578 or equivalent
White caps for 16 mm culture tubes, VWR Cat #60828-760 or equivalent
Blood serum filters, 6.×16 mm, VWR Cat #28295-556 or equivalent The following method was used to quantitate residual chloride amounts in fluorescein using potentiometric silver nitrate titration, an automatic titrator and a silver electrode.

(1) Reagent Solution Preparation, Ammonium Hydroxide (5N)

To purified water (~600 mL), concentrated ammonium hydroxide (~338 mL) was added and diluted to 1000 mL with purified water. This solution was used for the autotitrator to rinse and store the silver electrode.

(2) Standardized Solution Preparation, Silver Nitrate, 0.10 N, Aqueous

Use 0.10 N silver nitrate commercially prepared as a solution with a certificate of analysis is preferred. If, however, a commercially certified solution of silver nitrate is not available, then silver nitrate (17.0 g) may be weighed and dissolved in purified water (1000 mL) and standardized. Potassium chloride reference standard (dry, 50 mg) was weighed and dissolved in purified water (~30 mL) in a titration cup. Nitric acid (1 mL) was added to this solution. The solution was titrated potentiometrically using a silver billet electrode. Each mL of 0.10 N of silver nitrate was equivalent to 7.455 mg of potassium chloride. The normality of the silver nitrate was calculated using the following equation: N $AgNO_3$=(mg KCl×Purity KCl)/(mL $AgNO_3$×74.55).

(3) Sample Preparation and Titration

Fluorescein raw material (2 g) was weighed into culture tubes (16×125 mm). Purified water (hot, 10 mL) was added. Nitric acid (1 mL) was added and all tubes were capped, shaken for 2 minutes and sonicated for 15 minutes. All tubes were centrifuged for 30 minutes (~3,000 rpm). The precipitant was separated from the supernatant using blood serum filters. The solution was decanted into a titration cup. The blood serum was rinsed and filtered using purified water (5 mL portions). The rinses were poured into the titration cup. The blood serum filters were removed and discarded. The above procedure was repeated a second time except that all tubes were capped and shaken for 1 minute, and all tubes were centrifuged for 20 minutes (~3,000 rpm). The solutions from the first and the second extracts were combined and the serum filter was rinsed with purified water. The combined solution was titrated with 0.10 N Ag $NO_3$ to its potentiometric end point. The titration parameters include using a wash cycle (5N ammonium hydroxide) and a rinse cycle (5N ammonium hydroxide) after each sample. A list of parameters is shown below.

(4) Calculations $$\text{Percent Chloride} = \frac{(V) \times (N) \times 35.453 \times 100}{W}$$

V=Volume of 0.10 N $AgNO_3$ titrated
N=Normality of $AgNO_3$ titrant
35.453=Molecular weight of chloride
W=Weight of fluorescein example taken

TABLE 9

Residual Chloride

| Sample | Residual Chloride |
|---|---|
| 1 | 0.023% |
| 2 | 0.018% |
| 3 | <0.01% |
| 4 | <0.01% |

EXAMPLE 5

In this procedure, a solution of fluorescein raw material was prepared in methanol and separated from its related-substances using a high performance liquid chromatography (HPLC) system, gradient mobile phase programming, and a C-18 column. The related-substances were quantitated against a 1% solution of fluorescein reference standard. An ultraviolet HPLC detector was used to measure the peak responses at a wavelength of 280 nm. Mobile Phase A is 0.01M Ammonium Acetate, 10% Methanol/90% Water, and 0.5% Acetic Acid. Mobile Phase B is 0.01M Ammonium Acetate, 100% Methanol; 0.5% Acetic Acid. The reference standard was a 0.5 mg/mL solution of fluorescein in methanol, diluted to a final concentration of 0.005 mg/mL in methanol, or 1% of the sample final theoretical concentration of 0.5 mg/mL of fluorescein prepared similarly. A high-performance liquid chromatography system capable of programmed gradient operation was used, with an HPLC UV/VIS detector and the ability to monitor 280 nm. Column: 3.9×150 mm Waters Symmetry C-18 column, 5 μm, (or equivalent) capable of at least 20,000 plates/column for fluorescein. Flow Rate: 0.6 mL/min. The Gradient Program was as follows:

| Time (min) | % Mobile Phase A | % Mobile Phase B |
|---|---|---|
| 0 | 80% | 20% |
| 60 | 20% | 80% |
| Column wash: | | |
| 61 | 0% | 100% |
| 66 | 0% | 100% |
| Equilibration: | | |
| 67 | 80% | 20% |

Using peak areas, the percent concentration of known and unknown impurities equal to or greater than 0.025% were calculated, as shown in the calculation section below. Although the limit of quantitation for this method is 0.025%, impurities are generally reported at concentrations ≧0.05%. Nine impurities were found in the analysis of fluorescein and their molecular weights were determined by LC/MS. Their proposed structures are presented in FIG. 8. Impurity H was found as two diastereomers, H-1 and H-2. Typical relative retention times (RRT), capacity factors (k'), and gradient composition at time of elution (% B) for the impurities identified in the fluorescein lots cited in this procedure using this chromatographic method are as follows:

| | RRT | k' | B (%) |
|---|---|---|---|
| Impurity A | 0.75 | 11.1 | 43.0 |
| Impurity D | 1.19 | 18.2 | 56.5 |
| Impurity F | 1.23 | 18.8 | 57.7 |
| Impurity H-1 | 1.68 | 26.0 | 71.0 |
| Impurity H-2 | 1.71 | 26.5 | 72.0 |

Figure 6:
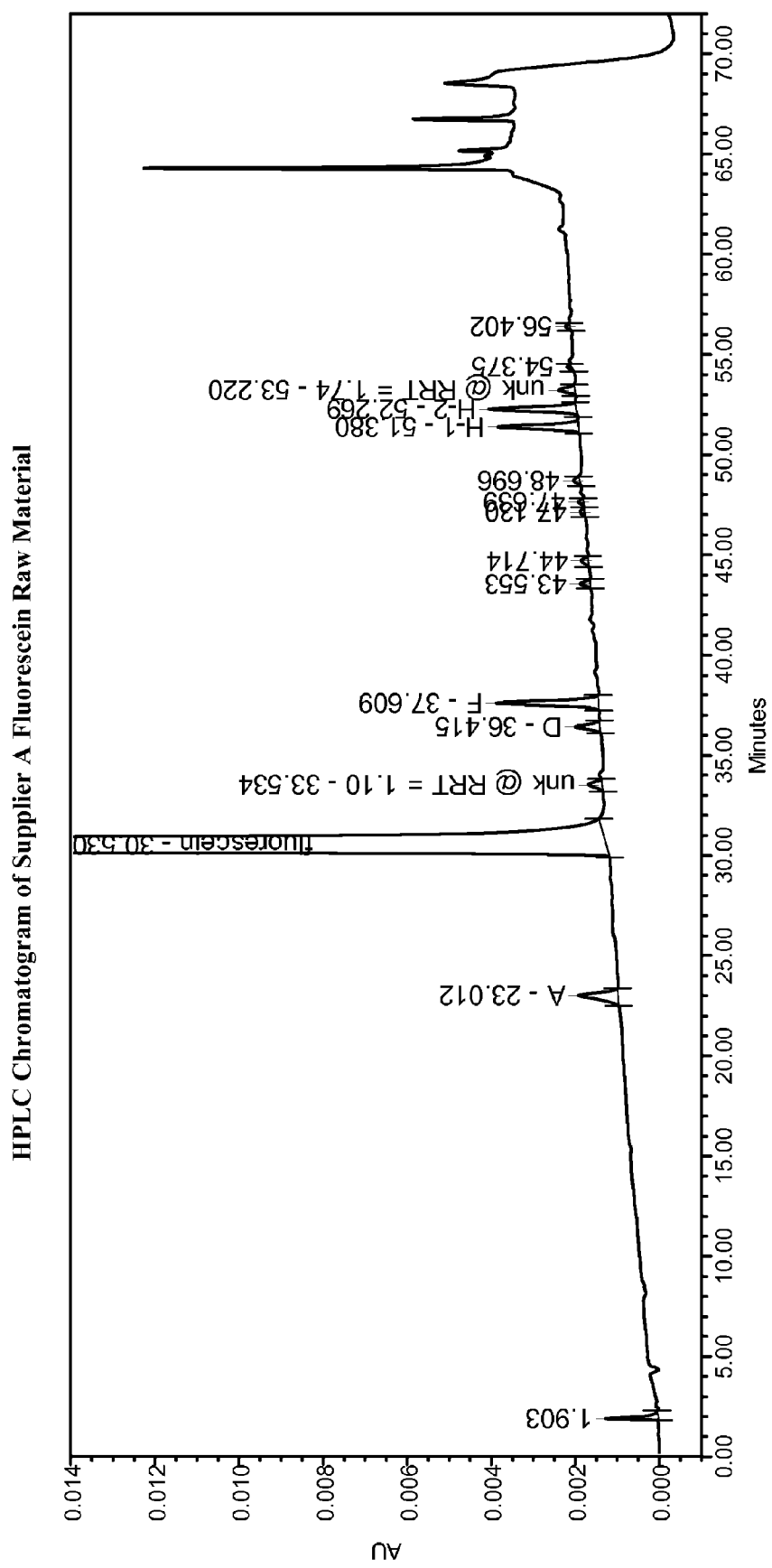
FIG. 6 is an HPLC chromatogram of Supplier A Fluorescein Raw Material as described in Example 5.

A peak in the fluorescein chromatogram may be identified as related substance A, D, F, H-1 or H-2 if the relative retention times, capacity factor and approximate mobile phase composition of the peak correspond to the related substances listed above. However, each of the relative retention time values can vary by approximately 0.02 between chromatographic systems. Modifications to the chromatographic system may also impact the values listed above. Although Impurities B, C, E and G were not identified in the four fluorescein lots assayed here, prior LC/MS analysis of Supplier A fluorescein suggests that Impurities B, C, E and G would have approximate RRT's of 1.09, 1.11, 1.20, and 1.44. Two unknown impurities, with RRT's of 1.10 and 1.74, respectively, were present in the four lots of fluorescein raw material reported in this document. Their concentrations were between 0.025% and 0.05%. It is possible that the unknown peak at RRT=1.10 could be either Impurity B or C. A chromatogram of a fluorescein raw material sample is shown in FIG. 6. Diacetylfluorescein has been observed in fluorescein drug substance and appears at a retention time relative to fluorescein of 1.35.

Figure 7:
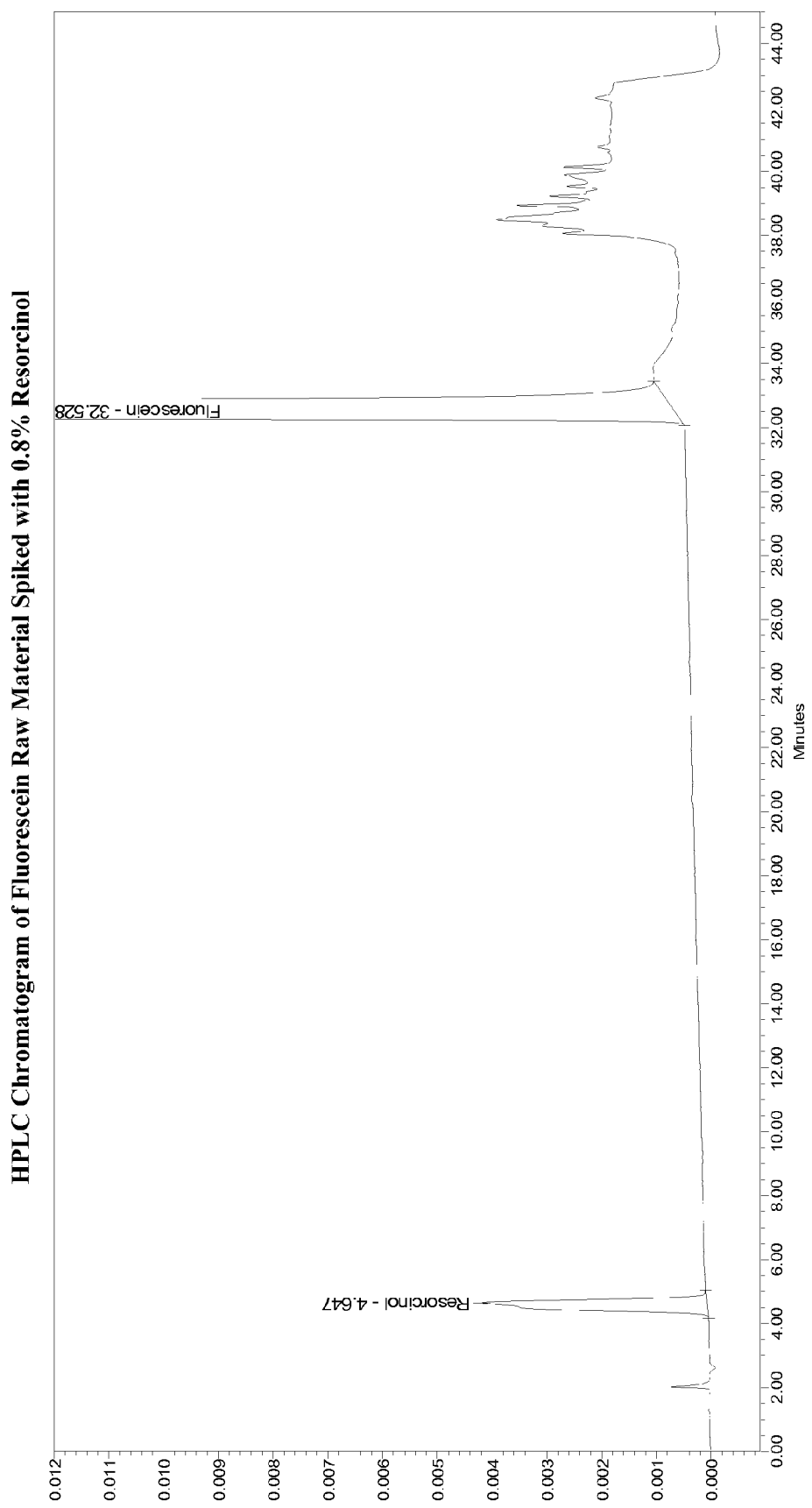
FIG. 7 is an HPLC chromatogram of Fluorescein Raw Material Spiked with 0.8% Resorcinol as described in Example 5.

Resorcinol is a known common impurity of fluorescein. Resorcinol is used as a starting material in the synthesis of fluorescein and is a potential degradation product. Resorcinol has been found to elute at a RRT of 0.14, k' of 2.9, and % B of 24.6 as presented above. Resorcinol may be observed to elute as an unresolved doublet on occasion. A chromatogram of fluorescein drug substance containing resorcinol is presented in FIG. 7.

Any nonrelated peaks (i.e., solvent front, system peaks) plus resorcinol were identified and omitted from the following calculations. Resorcinol eluted at RRT about 0.14 (see FIG. 7). The percent concentrations for each related substance were calculated as shown below.

$$\% \text{ Related Substances} = \frac{\text{Related Substance Area}}{\text{Standard Area}} \times \frac{\text{Standard Conc}}{\text{Sample Conc}} \times 100$$

$$\% \text{ Total Related Substances} = \sum (\text{Individual Impurities} \geq 0.025\%)$$

Calculate the total impurities by summing impurities with a concentration of 0.025% or above.

Calculate the relative retention according to the following formula:

$$RRT = \frac{t_i}{t_f}$$

$t_i$=the retention time of the impurity peak $t_f$=the retention time of the fluorescein peak The limit of quantitation for the method was established as 0.127 µg/mL of fluorescein (0.025% of the sample preparation concentration). The limit of detection was determined to be 0.05 µg/mL of fluorescein (0.01% of the sample preparation concentration).

Four lots of Supplier A fluorescein raw material were analyzed using this method. Seven impurities were detected and five impurities (A, D, F, H-1 and H-2) were identified. The total percent of reportable impurities ($\geq$0.025%) ranged between 0.2% and 0.7%. The results are listed in Table 10 below.

In an alternative to this procedure, the diluent for the sample and standard preparations are changed to permit simultaneous analysis of resorcinol and other related substance impurities. To prepare the diluent, first dissolve 0.77 g of ammonium acetate in 1000 mL of water, adjust pH to 3.9 with acetic acid, then add equal volumes of ammonium acetate buffer and methanol. After initially dissolving fluorescein in methanol at a ratio of 50 mg to 15 mL, this diluent is then used instead of methanol to dilute standards and samples as in the procedure described in Example 5, and the blank is changed as well to diluent from methanol. Protect the fluorescein standard and sample preparations from light after dilution with the diluent. Typical relative retention times (RRT) for resorcinol and phthalic acid are as follows:

|  | RRT | k' | B (%) |
|---|---|---|---|
| Resorcinol | 0.13 | 1.21 | 24.2% |
| Phthalic Acid | 0.16 | 1.53 | 24.9% |

An RRF (Relative Response Factor) may also be added to the calculation for the impurities, where the RRF represents the response relative to fluorescein.

| Impurity | RRF[1] |
|---|---|
| Resorcinol | 1.7 |
| Phthalic Acid | 2.6 |
| Impurity A | 0.43 |
| Impurity D | 1.0 |
| Impurity F | 1.0 |
| Impurity H-1 | 1.0 |
| Impurity H-2 | 1.0 |

[1]The relative response factors for impurities D, F, H-1, and H2- have not been determined. Their relative response factors are assumed to be 1.0.

The percent concentrations for each related substance can be calculated as shown below:

$$\% \text{ Related Substances} = \frac{\text{Related Substance Area}}{\text{Standard Area}} \times \frac{\text{Standard Conc}}{\text{Sample Conc}} \times RRF \times 100$$

TABLE 10

HPLC Assay Results for Supplier A Fluorescein Raw Material

| Lot Reference | Impurity A (%) | Unknown at RRT 1.10[a] (%) | Impurity D (%) | Impurity F (%) | Impurity H-1 (%) | Impurity H-2 (%) | Unknown at RRT 1.74 (%) | Total Impurity (%) |
|---|---|---|---|---|---|---|---|---|
| A | 0.1 | 0.03 | 0.05 | 0.2 | 0.1 | 0.1 | 0.03 | 0.7 |
| B | 0.03 | <0.025 | 0.03 | 0.05 | 0.05 | 0.06 | <0.025 | 0.2 |
| C | 0.05 | <0.025 | 0.04 | 0.1 | 0.1 | 0.1 | 0.04 | 0.5 |
| D | 0.04 | <0.025 | 0.04 | 0.07 | 0.09 | 0.1 | 0.03 | 0.4 |

The limit of quantitation of the method is 0.025%.
The limit of detection of the method is 0.01%.
[a]Peak at RRT 1.10 is probably Impurity B or C

EXAMPLE 6

An investigation was conducted to determine the identity of fluorescein-related substance impurities. Samples of fluorescein were analyzed for the presence and concentration of impurities. Identification analysis was conducted by high performance liquid chromatography/mass spectrometry (LC/MS).

Figure 9:
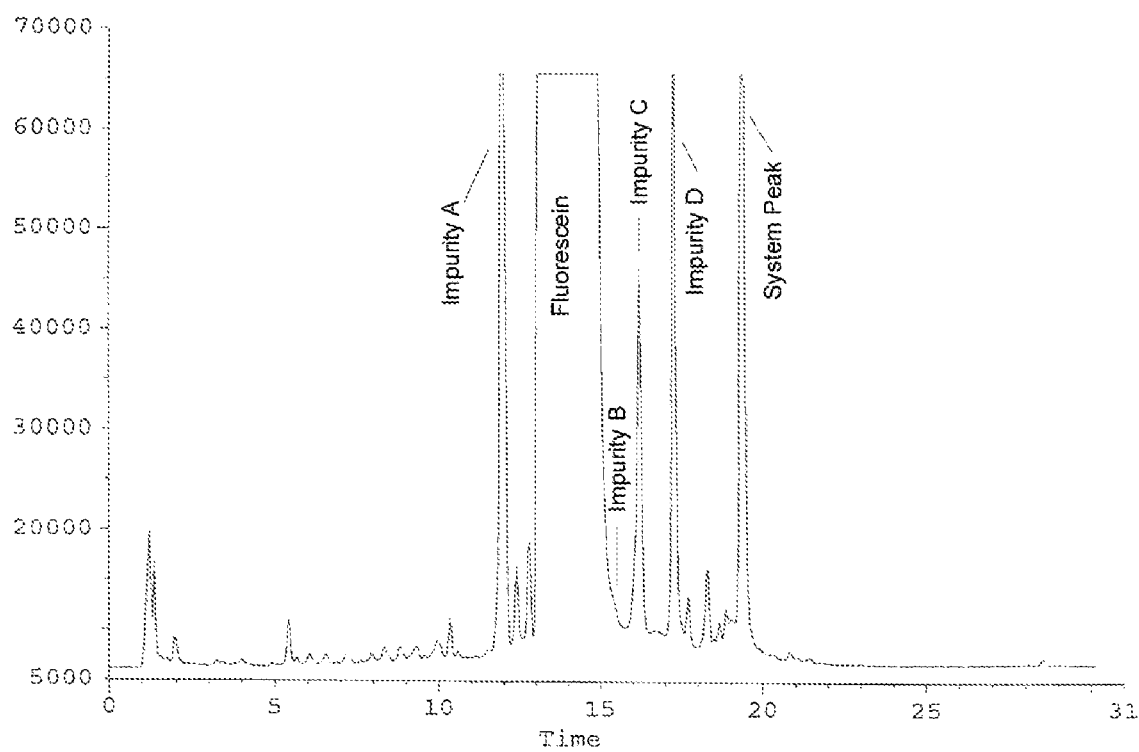
FIG. 9 is a representative HPLC Chromatogram of fluorescein from the LC/MS system.
Figure 10A:
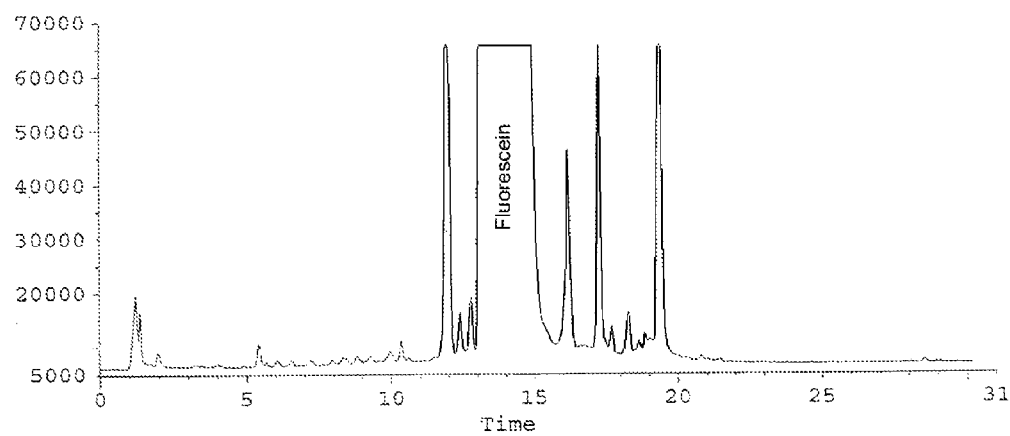
FIG. 10 is: (a) a chromatogram of fluorescein with UV detection; and (b) a thermospray mass spectrum of the HPLC peak of fluorescein sampled at 13.65-14.45 minutes.
Figure 10B:
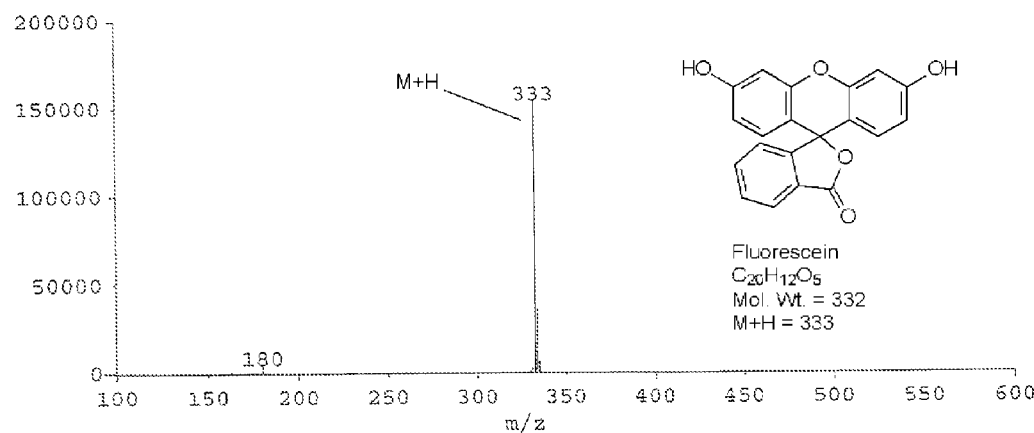

A representative HPLC chromatogram from the LC/MS system is reproduced in FIG. 9. Fluorescein produced the major peak in the chromatogram. The thermospray mass spectrum of fluorescein, shown in FIG. 10(b), produced a M+H molecular ion at m/z 333 which is consistent with the molecular weight of 332.

Figure 11A:
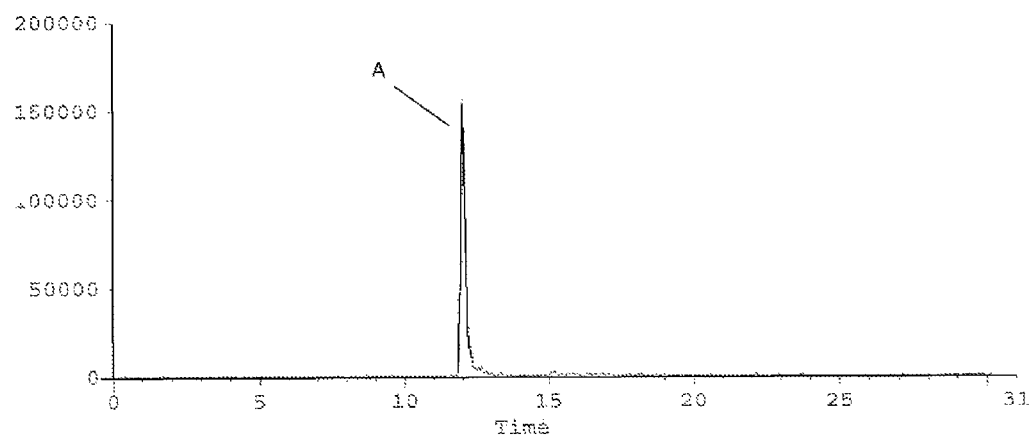
FIG. 11 is: (a) a chromatogram of Impurity A in fluorescein with mass selective detection at m/z 259 using the mass spectrometer; and (b) a thermospray mass spectrum of the HPLC peak of Impurity A sampled at 11.95-12.05 minutes.
Figure 11B:
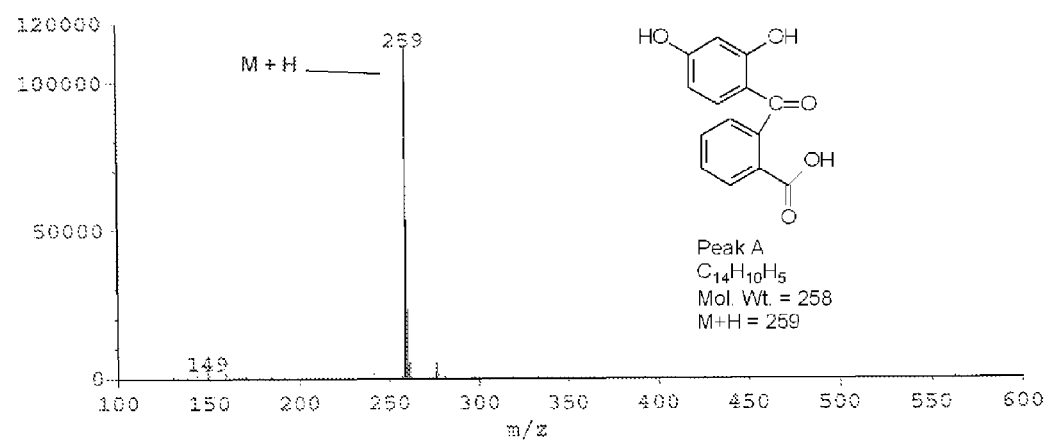

The thermospray mass spectrum of Impurity A, as shown in FIG. 11(b), produced an M+H molecular ion at m/z 259, indicating a molecular weight of 258. The structure proposed in FIG. 8 for Impurity A, [2-(2',4'-dihdyroxybenzoyl)benzoic acid], has been previously reported as an impurity in fluorescein preparations.

Figure 12A:
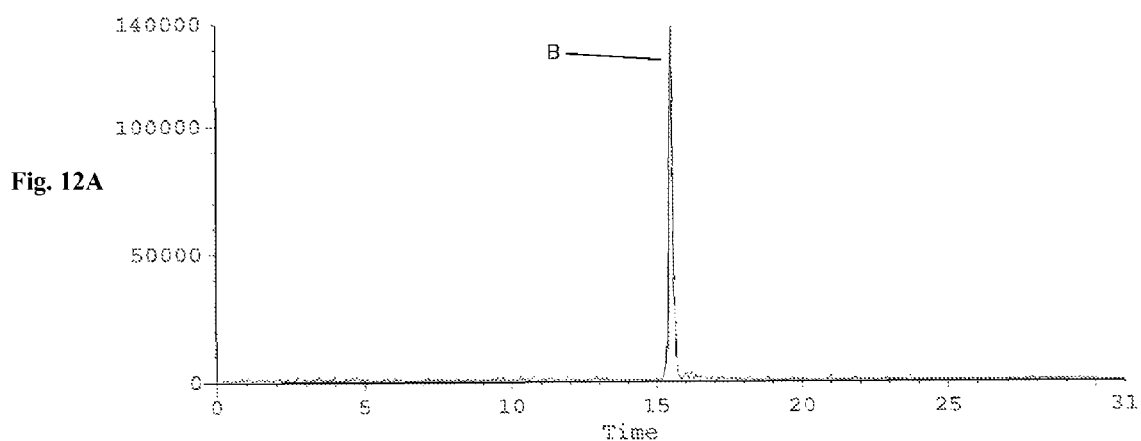
FIG. 12 is: (a) a chromatogram of Impurity B in fluorescein with mass selective detection at m/z 285 using the mass spectrometer; and (b) a thermospray mass spectrum of the HPLC peak of Impurity B sampled at 15.45-15.55 minutes.
Figure 12B:
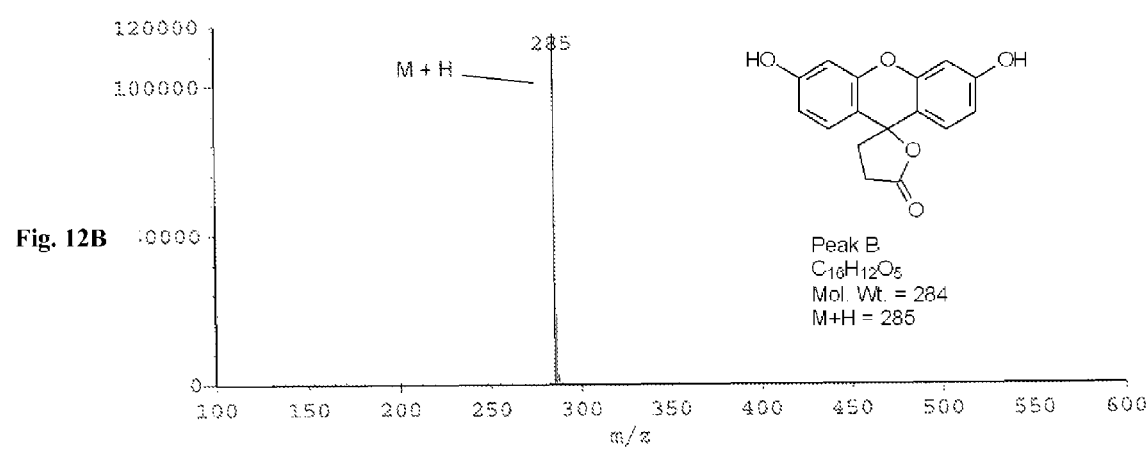

The thermospray mass spectrum of Impurity B, as shown in FIG. 12(b), indicates an M+H molecular ion at m/z 285, suggesting a molecular weight of 284. A molecular weight of 284 may correspond to elemental formulas of $C_{15}H_8O_6$, $C_{16}H_{12}O_5$, or $C_{17}H_{18}O_4$. A proposed structure shown for Impurity B in FIG. 8 may arise from the reaction of resorcinol with succinic acid (as an impurity in the phthalic acid precursor for fluorescein).

Figure 13A:
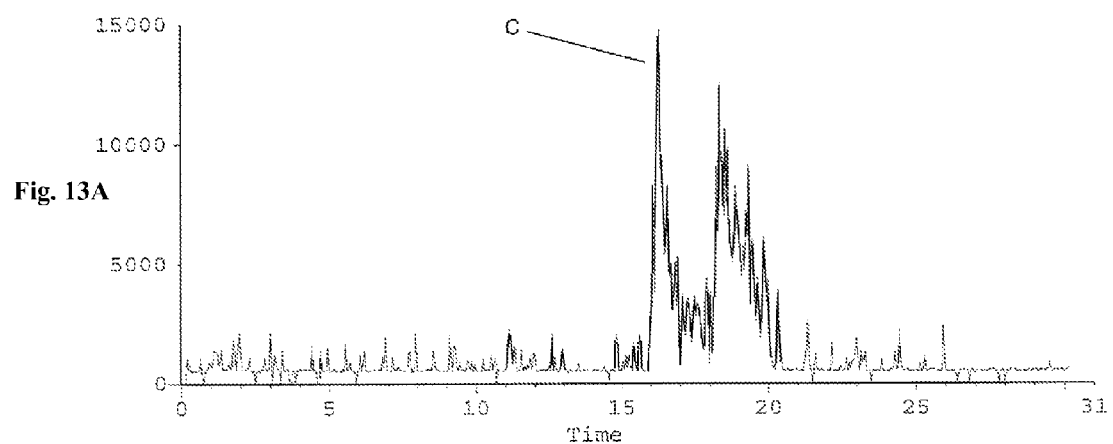
FIG. 13 is: (a) a chromatogram of Impurity C in fluorescein with mass selective detection at m/z 347 using the mass spectrometer; and (b) a thermospray mass spectrum of the HPLC peak of Impurity C sampled at 16.10-16.50 minutes.
Figure 13B:
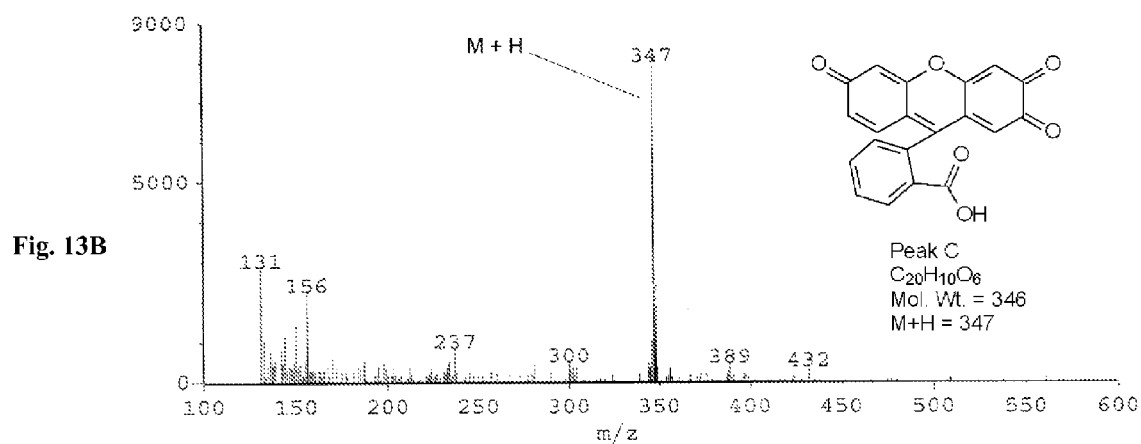

The thermospray mass spectrum of Impurity C, as shown in FIG. 13(b), indicates an M+H molecular ion at m/z 347. This represents a molecular weight of 346, and corresponds to a gain of 14 mass units over fluorescein.

Figure 14A:
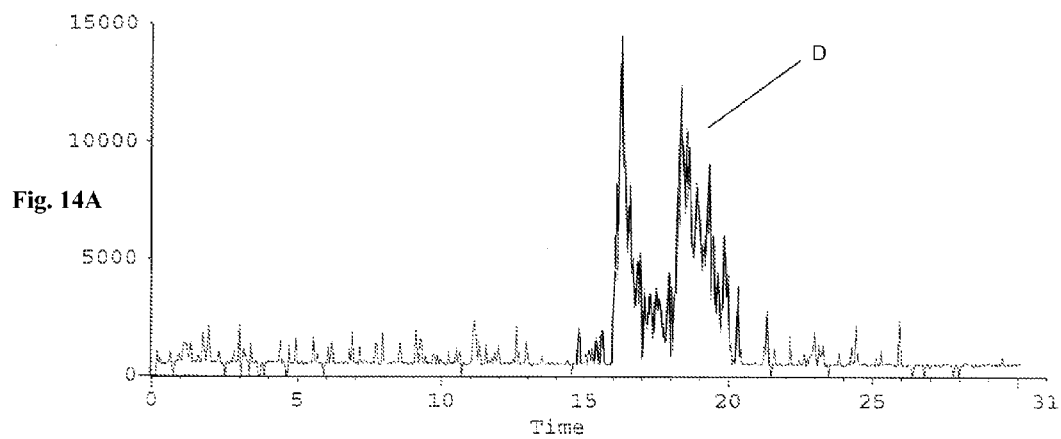
FIG. 14 is: (a) a chromatogram of Impurity D in fluorescein with mass selective detection at m/z 347 using the mass spectrometer; and (b) a thermospray mass spectrum of the HPLC peak of Impurity D sampled at 18.20-18.65 minutes.
Figure 14B:
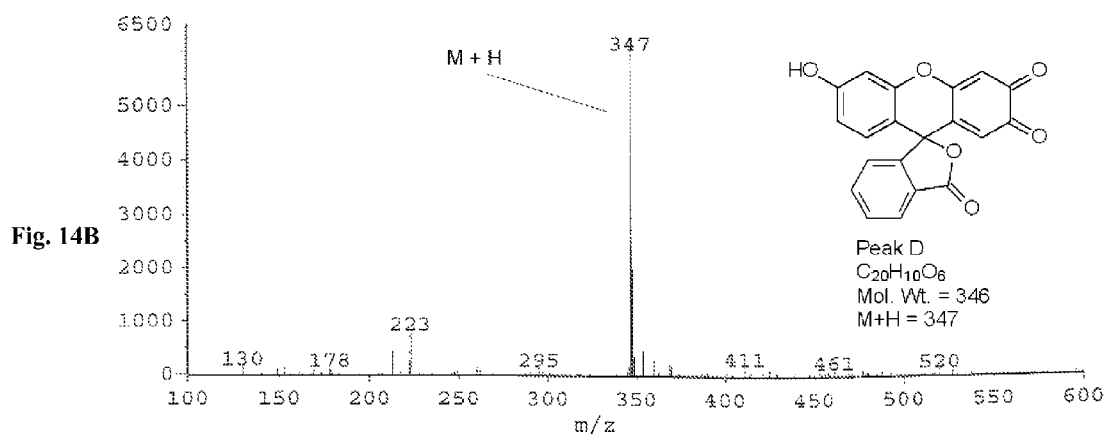

The thermospray mass spectrum of Impurity D, as shown in FIG. 14(b), also produced an M+H molecular ion at m/z 347, which is likely an isomer of Impurity C. The structures proposed for Impurities C and D are tautomers of each other, both being quinine-type oxidation products of fluorescein.

Figures 15A, 15B:
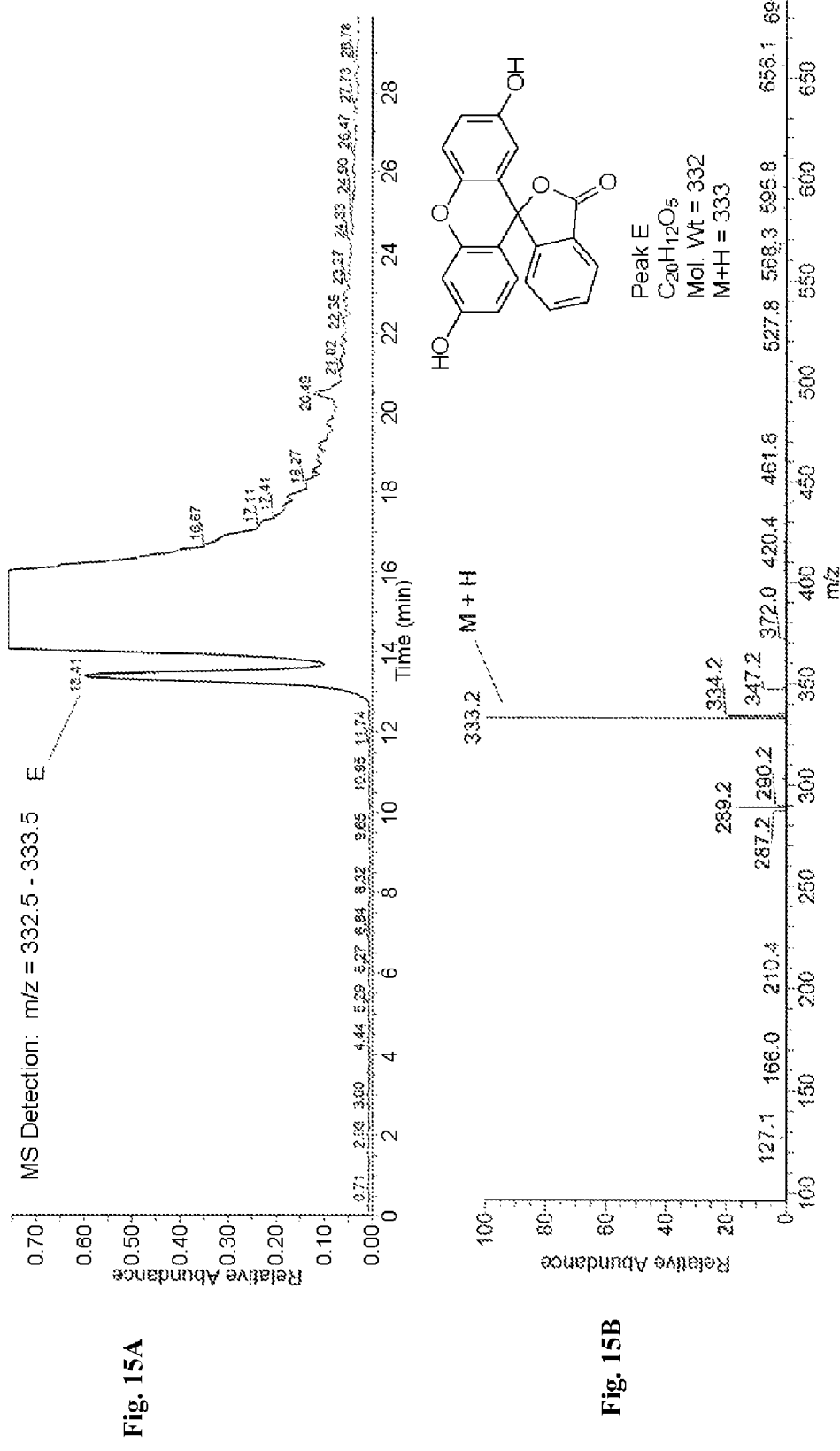
FIG. 15 is: (a) a chromatogram of Impurity E in fluorescein with mass selective detection at m/z 333 using the mass spectrometer; (b) is an APCI mass spectrum of the HPLC peak of Impurity E sampled at 13.23-13.52 minutes; (c) a chromatogram of Impurity E in fluorescein with detection by the total absorbance scan from 220-500 nm; and (d) a UV-Vis spectrum of the Impurity E peak.
Figure 15C:
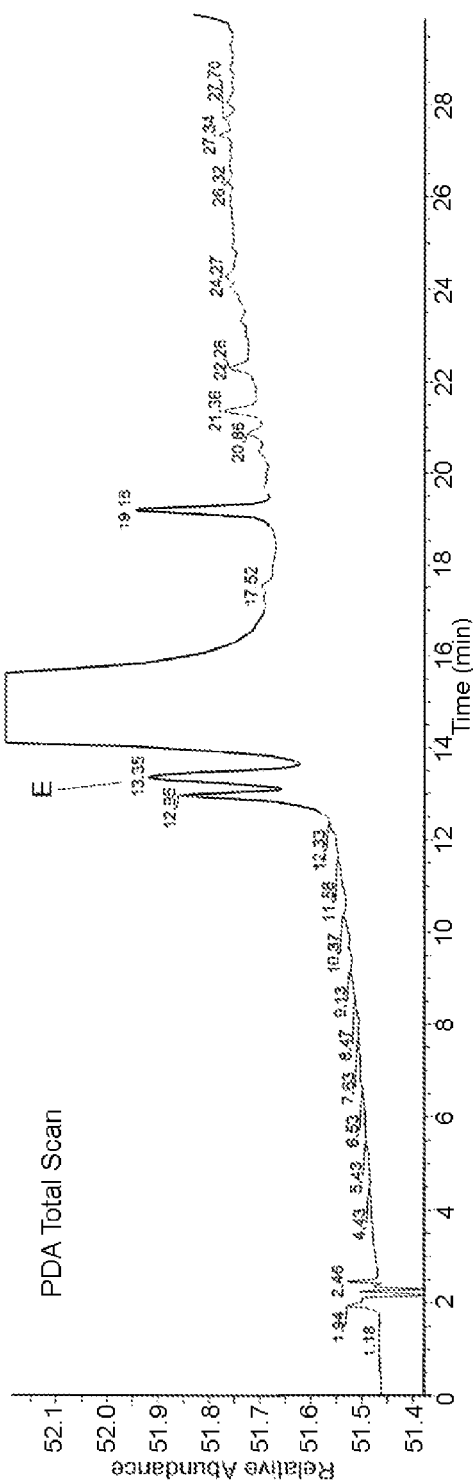
Figure 15D:
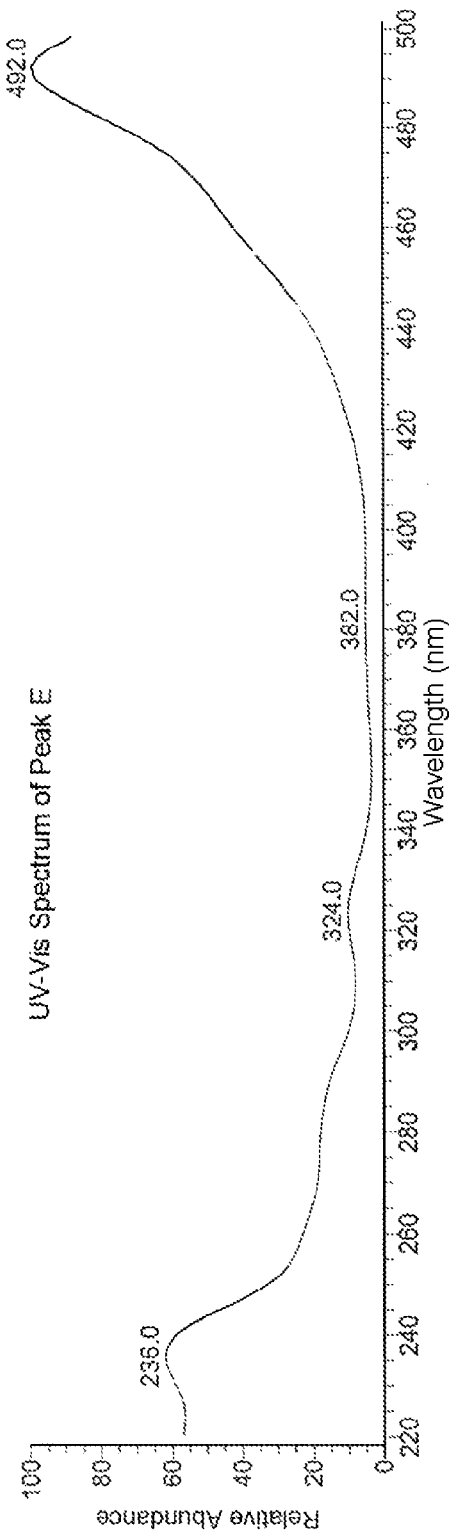

The APCI of Impurity E, as shown in FIG. 15(b), produced an M+H molecular ion at m/z 333 M+H, suggesting a molecular weight of 332, and a UV spectrum with a $UV_{max}$ at 492. Thus, it appears that Impurity E may be a positional isomer of fluorescein.

Figure 16C:
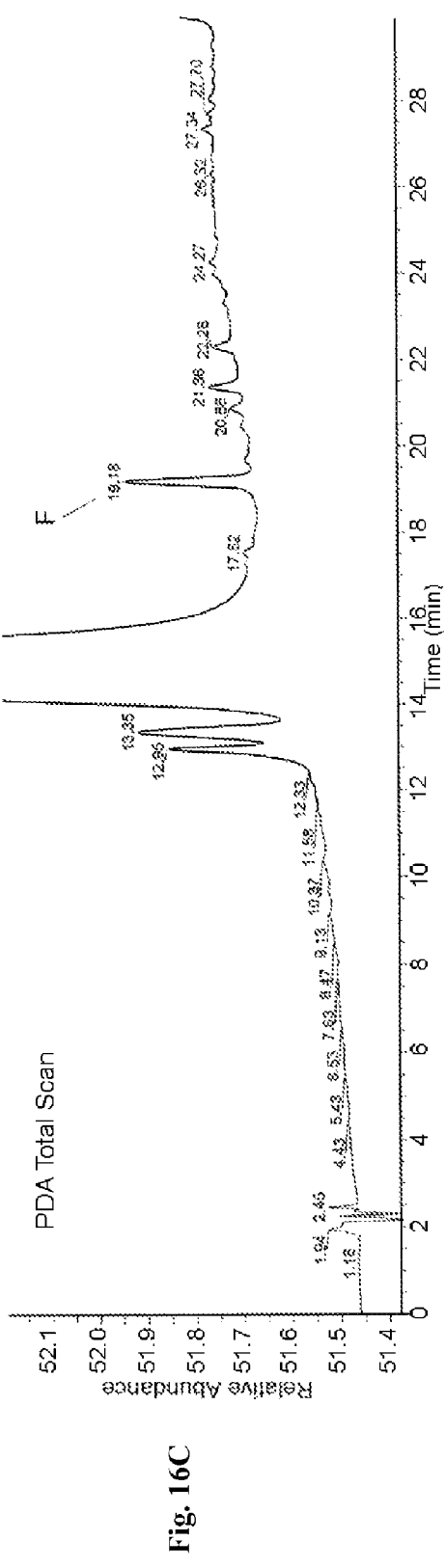
FIG. 16 is: (a) a chromatogram of Impurity F in fluorescein with mass selective detection at m/z 425 using the mass spectrometer; (b) is an APCI mass spectrum of the HPLC peak of Impurity F sampled at 19.10-19.32 minutes; (c) a chromatogram of Impurity F in fluorescein with detection by the total absorbance scan from 220-500 nm; and (d) a UV-Vis spectrum of the Impurity F peak.
Figure 16D:
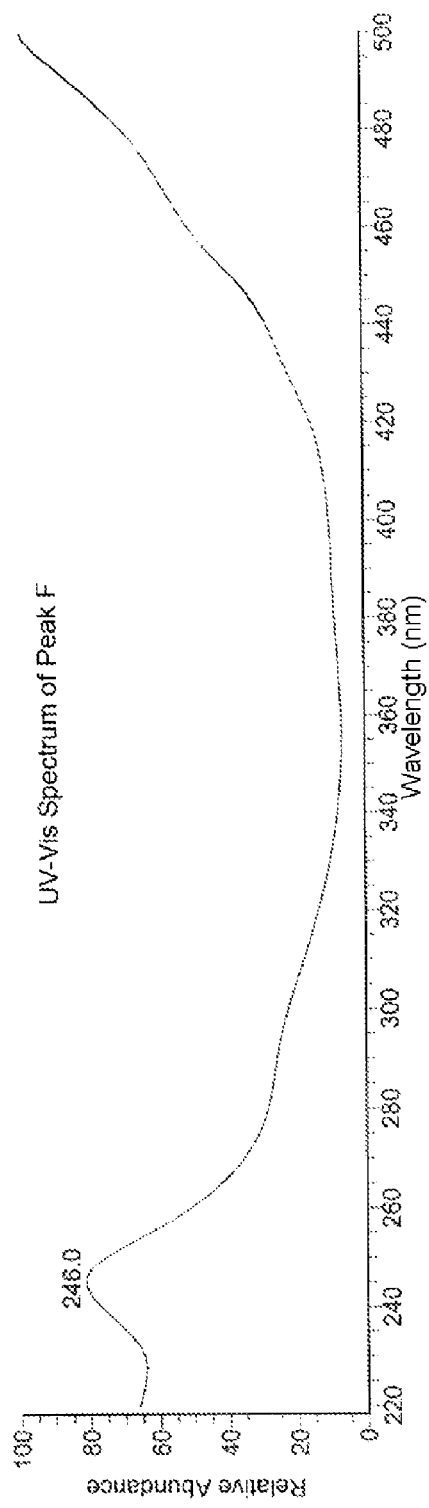

The APCI of Impurity F, as shown in FIG. 16(b), produced an M+H molecular ion at m/z 425 suggesting a molecular weight of 424, and a $UV_{max}$ greater than 400 nm. The spectra appears to be consistent with an additional resorcinol molecule added to the parent compound. Thus, Compound F may form from three resorcinols, while the parent may form from two resorcinols.

Figure 17C:
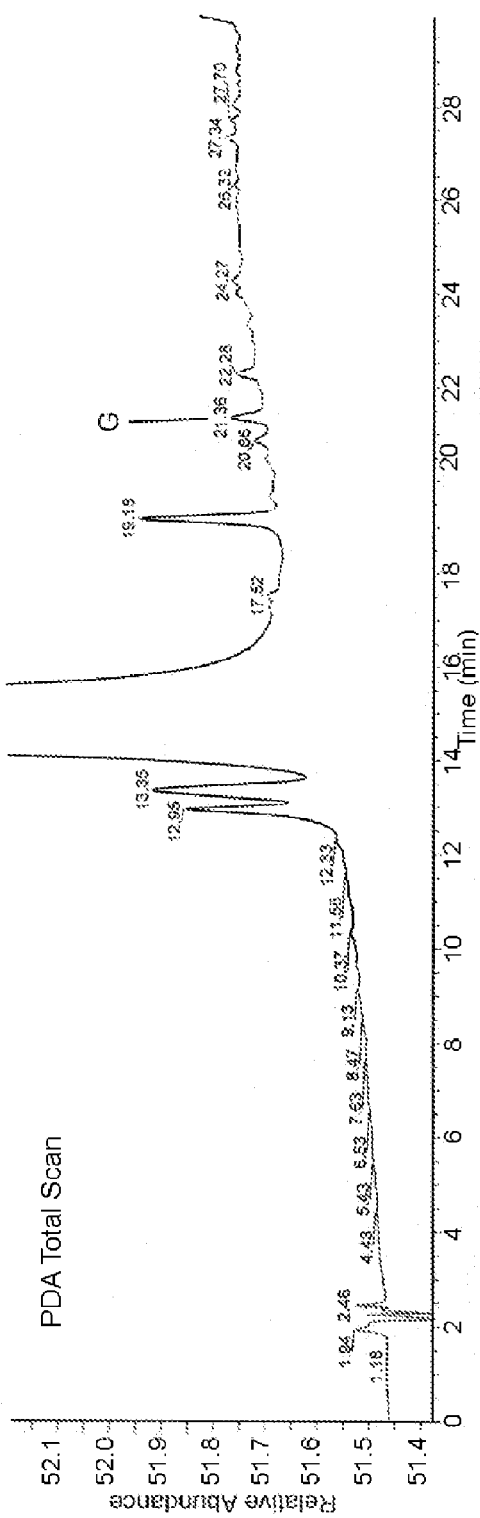
FIG. 17 is: (a) a chromatogram of Impurity G in fluorescein with mass selective detection at m/z 375 using the mass spectrometer; (b) is an APCI mass spectrum of the HPLC peak of Impurity G sampled at 21.27-21.54 minutes; (c) a chromatogram of Impurity G in fluorescein with detection by the total absorbance scan from 220-500 nm; and (d) a UV-Vis spectrum of the Impurity G peak.
Figure 17D:
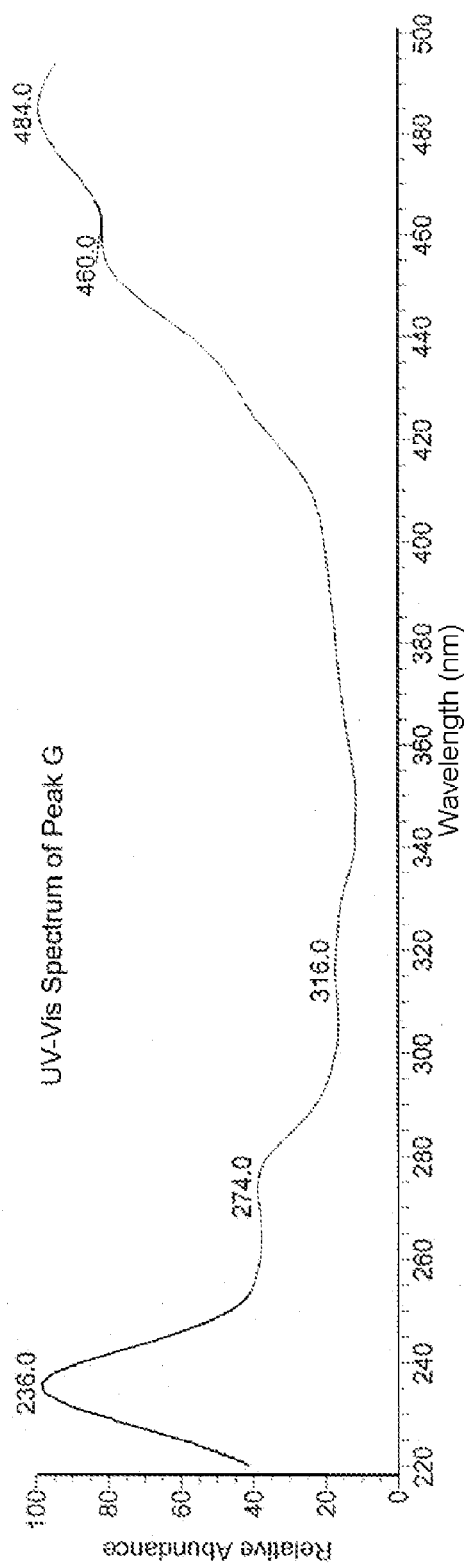

The APCI of Impurity G, as shown in FIG. 17(b), produced an M+H molecular ion at m/z 375, suggesting a molecular weight of 374, and a $UV_{max}$ at 484 nm. Both spectra and the lipophilicity appeared to be consistent with the acetate ester of fluorescein.

Figure 18A:
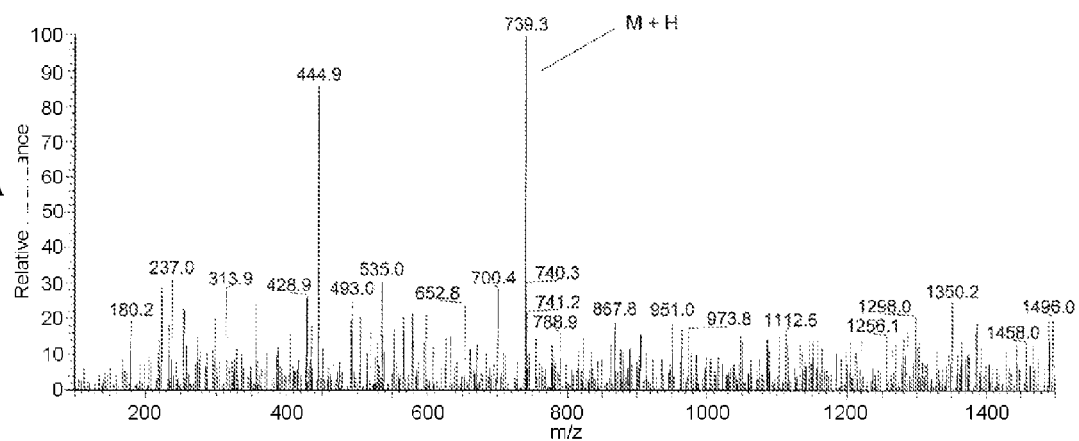
FIG. 18 is: (a) an APCI mass spectrum of the HPLC peak of Impurity H-1 sampled at 51.75-51.85 minutes; and (b) a chromatogram of Impurity H-1 in fluorescein with detection by total absorbance scan from 220-500 nm.
Figure 18B:
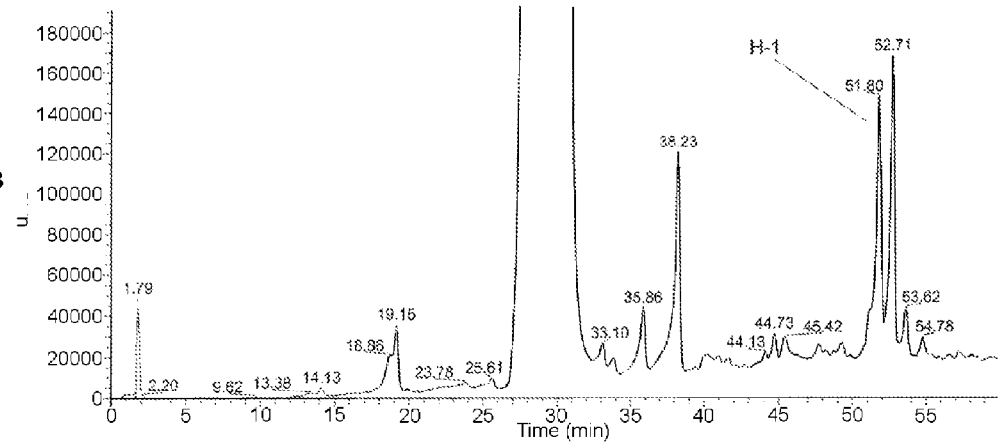
Figure 19A:
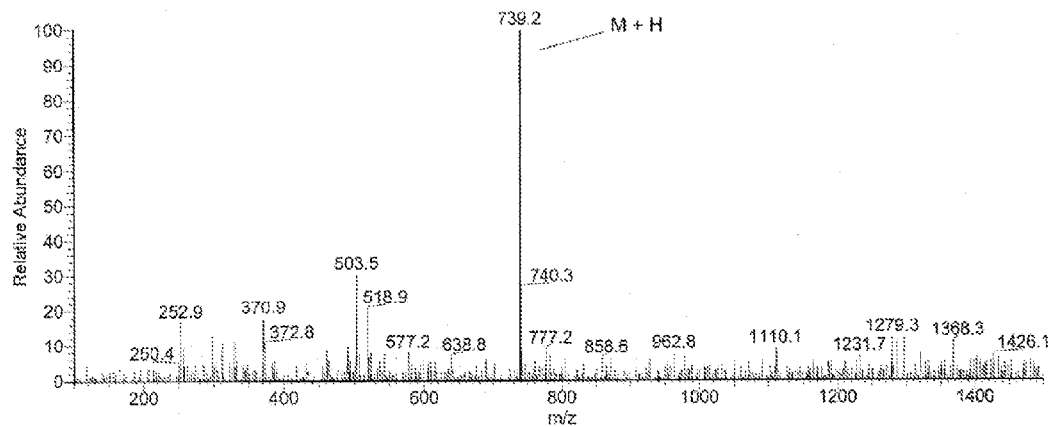
FIG. 19 is: (a) an APCI mass spectrum of the HPLC peak of Impurity H-2 sampled at 52.67-52.79 minutes; and (b) a chromatogram of Impurity H-2 in fluorescein with detection by total absorbance scan from 220-500 nm.
Figure 19B:
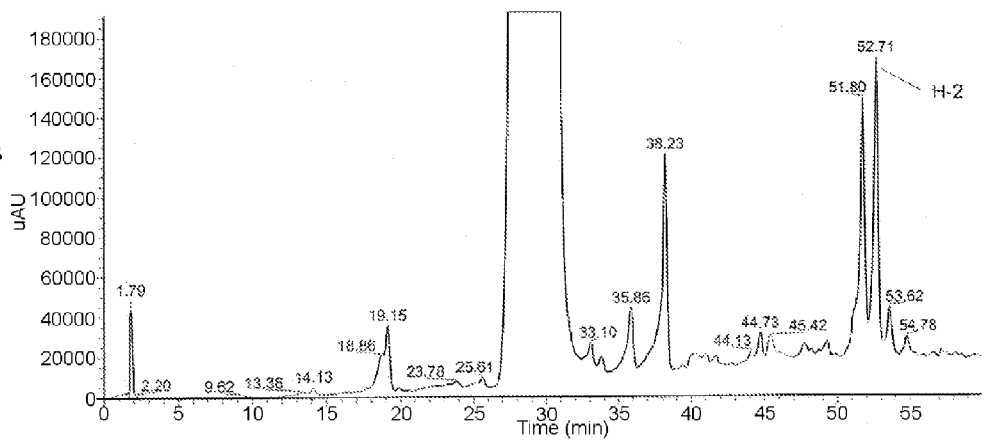
Figure 20:
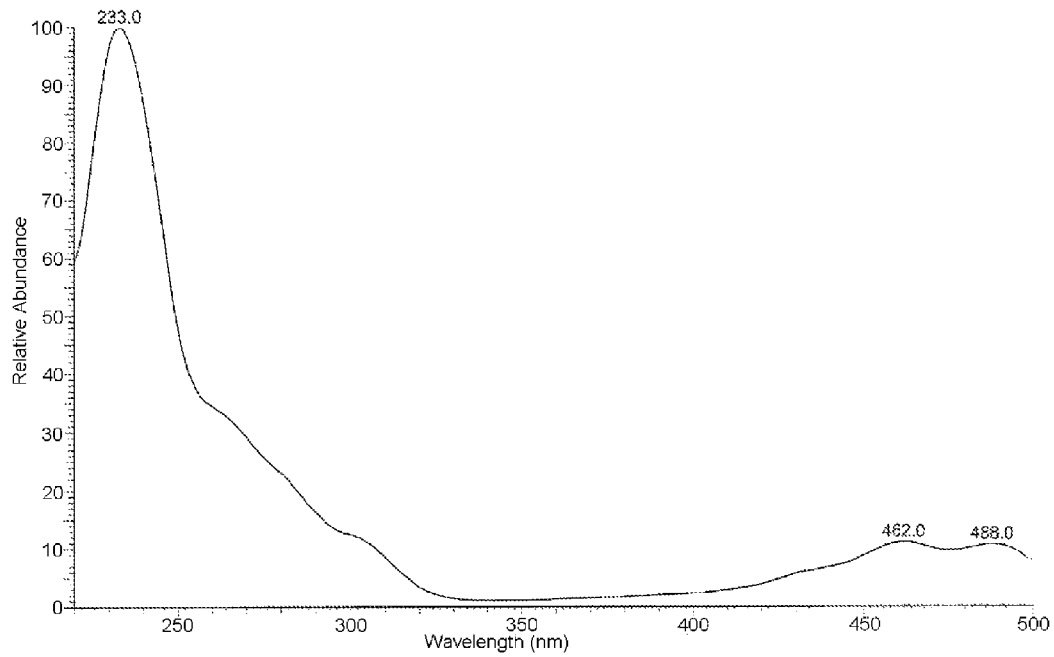
FIG. 20 is the UV-Vis absorbance scan of Impurity H-2.

The APCI of Impurities H-1 and H-2, as shown in FIGS. 18(a) and 19(a), produced an M+H molecular ion at m/z 739 for both compounds, suggesting a molecular weight of 738 for each. The UV-Vis absorbance spectrum of both compounds was the same, with an $UV_{max}$ at 233 nm, and weaker absorbance maxima at 462 and 488 nm. The absorbance spectrum of Impurity H-2 is shown in FIG. 20.

EXAMPLE 7

Preparation of Fluorescein for Injection, or Fluorescite 25%

In 60% of the required water for injection in the compounding tank, the required amount of sodium hydroxide was dissolved and weighed. The fluorescein was added and dissolved. Additional water for injection was added if required to dissolve, but the volume was not brought to more than 90% of total volume. If fluorescein did not completely dissolve after 30 minutes stirring, proceeded to next step to adjust pH. The pH was adjusted to 9.4, which was done with sodium hydroxide 3N and/or hydrochloric acid IN. The mixture was stirred for 30 minutes at 180 R.P.M. The pH was rechecked. If less than 9.3 or greater than 9.5 readjusted pH to 9.4 with sodium hydroxide 3N and/or hydrochloric acid 1N. The sodium fluorescein solution was brought to volume with additional water for injection, and stirred for 15 minutes. The pH was rechecked as noted above. Using a nitrogen tank, the solution was pressure filtered through a series of three membrane filters with pore size of 5 microns, 0.8 microns, and 0.45 microns into a sterile filling tank. The pH of the product was rechecked using procedure noted above. A sample was aseptically withdrawn for laboratory testing. Product was filled in ampoules previously sterilized. To each ampoule was added 2.15 to 2.25 mL. Immediately after filling, the samples were tip-sealed or pull-sealed by standard methods. Each ampoule seal was tested during sterilization. The ampoules were sterilized by autoclaving at 121° C. for 20 minutes or longer depending on batch size. Inspected carefully for leaks. Each ampoule was individually inspected for particulate matter under optimum lighted conditions.

EXAMPLE 8

Preparation of Fluorescein for Injection, or Fluorescite 10%

As an alternative procedure for preparing fluorescein for injection, into a suitable stainless steel tank was added approximately 70%-75% of batch quantity of cool water for injection (approximately 30° C.). Fluorescein was added with mixing until suspension was complete. The initial pH was recorded. A sufficient quantity (approximately 7.5% of the total volume) of 7N sodium hydroxide was added, then further amounts of 7 N sodium hydroxide were added, with rechecking of the pH value after waiting for approximately 15 minutes between additions, until the pH was between 9.3-9.5 with a target of pH 9.4. If the pH was greater than 9.5, the pH was adjusted by adding IN hydrochloric acid to obtain the pH range of 9.3-9.5. After the pH range is reached, mixing was continued for not less than 15 minutes. The batch was brought to final weight with water for injection, and mixed for not less than 30 minutes. The pH was tested and adjusted with sodium hydroxide or hydrochloric acid as needed. The product was filled aseptically into sterile vials, with further inspection and testing according to standard operating procedures.

The specific embodiments highlighted here are not intended to be a catalog of all the embodiments of the invention. Further, those skilled in the art will recognize, or be able to ascertain using no more than routine experimentation, many equivalents to the embodiments of the invention. Such equivalents are intended to be encompassed by the following claims.

We claim:

1. A composition comprising fluorescein, wherein the composition does not contain any related-substance impurity at a concentration of greater than about 0.1% by weight.

2. The composition of claim 1 wherein the composition is substantially free of pyridine.

3. The composition of claim 1, wherein the composition does not contain any related-substance impurity at a concentration of greater than about 0.01% by weight.

4. The composition of claim 1, wherein the total amount of related-substance impurities present in the composition is less than about 0.6% by weight.

5. The composition of claim 4, wherein the total amount of related-substance impurities present in the composition is less than about 0.06% by weight.

6. The composition of claim 1, wherein the fluorescein has a color number of from about 0.015 to about 0.050 AUC.

7. The composition of claim 1, wherein the amount of residual chloride present in the composition is less than about 0.25% by weight.

8. A process for preparing fluorescein which comprises: (a) hydrolyzing diacetylfluorescein with sodium hydroxide to form fluorescein; (b) adding charcoal to the fluorescein in solution to form a fluorescein/charcoal mixture; (c) filtering the fluorescein/charcoal mixture to form a filtrate; (d) adding ethanol to the filtrate to obtain a higher proportion of ethanol than to water; (e) adjusting the pH to a level of from 1.0 to 2.5 using an acidic solution to form a precipitate; (f) filtering the solution to retain the precipitate; and (g) washing the precipitate with water and ethanol, wherein the precipitate is the fluorescein not containing any related-substance impurity at a concentration of greater than about 0.1% by weight.

9. The process of claim 8, wherein step (e) is conducted with cooling.

10. The process of claim 8, wherein step (e) is conducted during a period of from about 2 to about 4 hours.

11. Fluorescein prepared by the process of claim 8 wherein the fluorescein does not contain any related-substance impurity at a concentration of greater than about 0.1% by weight.

12. A method of determining the purity of a fluorescein composition which comprises: (a) obtaining a high-pressure liquid chromatogram of the composition; (b) identifying peaks in the chromatogram corresponding to related-substance impurities; and (c) taking area measurements of the peaks to determine a relative concentration thereof.

13. The method of claim 12, wherein the peaks have relative HPLC retention times of about 0.75, 1.19, 1.23, 1.68 and 1.71.

14. A pharmaceutical composition for use in angiography, comprising fluorescein wherein the composition does not contain any related-substance impurity at a concentration of greater than about 0.1% by weight and a vehicle for injection.

15. The composition of claim 14, wherein the composition is substantially free of pyridine.

16. The composition of claim 14, wherein the total amount of related-substance impurities present in the composition is less than about 0.6% by weight.

17. The composition of claim 14, wherein the composition has a color number of from about 0.015 to about 0.050 AUC.

18. The composition of claim 14, wherein the amount of residual chloride present in the composition is less than about 0.25% by weight.

19. A composition comprising fluorescein prepared by process of claim 8 wherein the composition does not contain any related-substance impurity at a concentration of greater than about 0.1% by weight.

20. A composition comprising fluorescein prepared by deacetylation of diacetylfluorescein wherein the composition does not contain any related-substance impurity at a concentration of greater than about 0.1% by weight.

* * * * *